US012753173B2

(12) United States Patent
Tong et al.

(10) Patent No.: US 12,753,173 B2
(45) Date of Patent: Oct. 6, 2026

(54) AMORPHOUS SUBSTANCES, CRYSTALS, PHARMACEUTICAL COMPOSITIONS, PREPARATION METHODS AND USES OF THIOHYDANTOIN COMPOUND OR PHARMACEUTICALLY ACCEPTABLE SALT THEREOF

(71) Applicant: SUZHOU KINTOR PHARMACEUTICALS, INC., Suzhou (CN)

(72) Inventors: Youzhi Tong, Suzhou (CN); Chun Deng, Suzhou (CN)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 377 days.

(21) Appl. No.: 18/690,032

(22) PCT Filed: Sep. 7, 2022

(86) PCT No.: PCT/CN2022/117515
§ 371 (c)(1),
(2) Date: Mar. 7, 2024

(87) PCT Pub. No.: WO2023/036171
PCT Pub. Date: Mar. 16, 2023

(65) Prior Publication Data

US 2025/0129062 A1 Apr. 24, 2025

(30) Foreign Application Priority Data

Sep. 8, 2021 (CN) ........................ 202111051462.2

(51) Int. Cl.

| | |
|---|---|
| ***C07D 417/14*** | (2006.01) |
| ***A61K 9/00*** | (2006.01) |
| ***A61K 9/06*** | (2006.01) |
| ***A61K 31/4439*** | (2006.01) |
| ***A61K 47/10*** | (2017.01) |
| ***A61K 47/18*** | (2017.01) |
| ***A61K 47/26*** | (2006.01) |
| ***A61K 47/32*** | (2006.01) |
| ***A61K 47/34*** | (2017.01) |
| ***A61K 47/44*** | (2017.01) |
| ***C07C 303/44*** | (2006.01) |
| ***C07C 309/35*** | (2006.01) |

(52) U.S. Cl.
CPC .......... *C07D 417/14* (2013.01); *A61K 9/0014* (2013.01); *A61K 9/06* (2013.01); *A61K 31/4439* (2013.01); *A61K 47/10* (2013.01); *A61K 47/18* (2013.01); *A61K 47/26* (2013.01); *A61K 47/32* (2013.01); *A61K 47/34* (2013.01); *A61K 47/44* (2013.01); *C07C 303/44* (2013.01); *C07C 309/35* (2013.01); *C07B 2200/13* (2013.01)

(58) Field of Classification Search
CPC ...... C07D 417/14; A61K 9/0014; A61K 9/06; A61K 31/4439; A61K 47/10; A61K 47/18; A61K 47/26; A61K 47/32; A61K 47/34; A61K 47/44; C07C 303/44; C07C 309/35; C07B 2200/13
See application file for complete search history.

(56) References Cited

U.S. PATENT DOCUMENTS

| | | |
|---|---|---|
| 2015/0291562 A1 | 10/2015 | Crew et al. |
| 2018/0099940 A1 | 4/2018 | Crew et al. |
| 2023/0054270 A1 | 2/2023 | Tong |

FOREIGN PATENT DOCUMENTS

| | | |
|---|---|---|
| CN | 106458993 A | 2/2017 |
| CN | 110506039 A | 11/2019 |
| CN | 110903345 A | 3/2020 |

(Continued)

OTHER PUBLICATIONS

Extended European Search Report issued in European Patent Application No. 22866634.3, dated Jul. 23, 2025.

(Continued)

*Primary Examiner* — Kamal A Saeed
*Assistant Examiner* — Quincy McKoy
(74) *Attorney, Agent, or Firm* — pH IP Law

(57) ABSTRACT

The present invention relates to amorphous substances, crystals, pharmaceutical compositions, preparation methods and uses of a thiohydantoin compound or pharmaceutically acceptable salt thereof. Specifically, provided are an amorphous substance of a compound of formula I, 1,5-naphthalene disulfonate thereof, an amorphous substance and two crystals (having crystal form A and crystal form B, respectively) of the 1,5-naphthalene disulfonate thereof, and corresponding pharmaceutical compositions, as well as preparation methods for the products above and corresponding pharmaceutical uses.

(I)

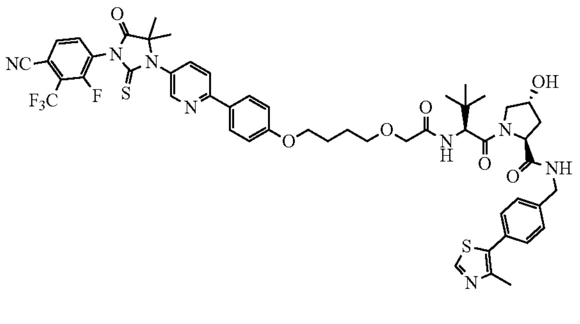

19 Claims, 9 Drawing Sheets

(56) References Cited

FOREIGN PATENT DOCUMENTS

| | | | |
|---|---|---|---|
| CN | 11212835 | A | 5/2020 |
| CN | 113387930 | A | 9/2021 |
| EP | 4119546 | A1 | 1/2023 |
| WO | WO 2016/1186666 | A1 | 7/2016 |
| WO | WO 2019/023553 | A1 | 1/2019 |
| WO | WO 2021/180160 | A1 | 9/2021 |

OTHER PUBLICATIONS

Hilfiker, R. et al., "Relevance of Solid-state Properties for Pharmaceutical Products," *Polymorphism: in the Pharmaceutical Industry*, (2006): 1-19.

Scott, D. E. et al., "Systematic Investigation of the Permeability of Androgen Receptor PROTACs," *ACS Medicinal Chemistry Letters*, 11 (2020): 1539-1547.

PCT International Search Report issued in International Patent Application No. PCT/CN2022/117515, mailed Dec. 5, 2022.

AMORPHOUS SUBSTANCES, CRYSTALS, PHARMACEUTICAL COMPOSITIONS, PREPARATION METHODS AND USES OF THIOHYDANTOIN COMPOUND OR PHARMACEUTICALLY ACCEPTABLE SALT THEREOF

CROSS-REFERENCE TO RELATED APPLICATIONS

This is a U.S. National Phase application based upon PCT Application No. PCT/CN2022/117515, filed Sep. 7, 2022, entitled "AMORPHOUS SUBSTANCES, CRYSTALS, PHARMACEUTICAL COMPOSITIONS, PREPARATION METHODS AND USES OF THIOHYDANTOIN COMPOUND OR PHARMACEUTICALLY ACCEPTABLE SALT THEREOF," which claims the right of priority of patent application no. 202111051462.2 titled "AMORPHOUS SUBSTANCES, CRYSTALS, PHARMACEUTICAL COMPOSITIONS, PREPARATION METHODS AND USES OF THIOHYDANTOIN COMPOUND OR PHARMACEUTICALLY ACCEPTABLE SALT THEREOF" and filed with the China Patent Office on Sep. 8, 2021, the entire contents of which are incorporated herein by reference in their entireties.

TECHNICAL FIELD

The present invention belongs to the technical field of pharmaceutical crystal chemistry, and in particular relates to amorphous substances of a thiohydantoin compound, amorphous substances and crystals of a pharmaceutically acceptable salt of the thiohydantoin compound, pharmaceutical compositions comprising the thiohydantoin compound, a method for preparing the thiohydantoin compound, and the use in the field of medicine.

BACKGROUND ART

Androgen receptor (AR) belongs to a family of nuclear hormone receptors that are activated by androgens. In the absence of androgens, AR is bound by heat shock protein 90 (Hsp90) in the cytosol. When an androgen binds to AR, its conformation changes to release AR from Hsp90 and an expose nuclear localization signal (NLS). The nuclear localization signal enables the transfer of AR into the nucleus, where AR functions as a transcription factor to promote the expression of genes responsible for male sex characteristics. AR deficiency can lead to androgen insensitivity syndrome.

The applicant has developed a bifunctional compound (CN 202110246427.X) in the early stage, in which the bifunctional compound (as shown in formula I) comprises an E3 ubiquitin ligase binding moiety; a target protein binding moiety that binds to androgen receptor (AR); and a linking moiety that links the E3 ubiquitin ligase binding moiety to the target protein binding moiety, the bifunctional compound can act as a degradant or an inhibitor of androgen receptor (AR). This bifunctional compound localizes the androgen receptor in proximity to ubiquitin ligase to achieve the degradation or inhibition of androgen receptor (AR). However, studies on polymorphs and pharmaceutical preparations of the bifunctional compound have not been reported in relevant literatures so far.

I

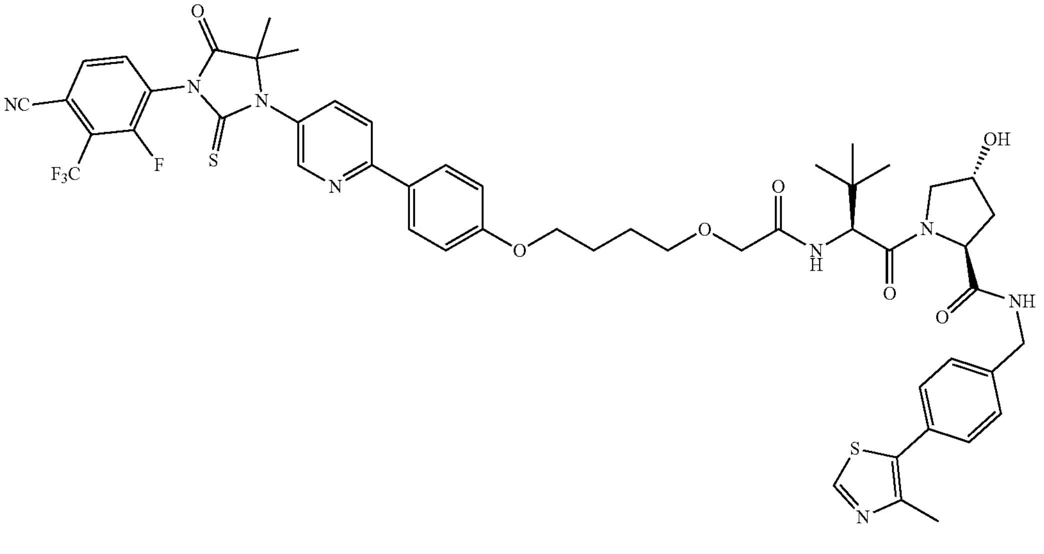

SUMMARY OF THE INVENTION

Problems to be Solved by the Invention

In order to ensure the physicochemical stability of drugs in the processes of production, processing and storage, an amorphous substance of a free alkali and an amorphous substance and two crystals of a pharmaceutically acceptable salt are obtained by in-depth study of different forms of a compound of formula I, and the corresponding preparation processes are operable, and provide scientific basis for clinical drug research. In addition, in order to facilitate the topical use of drugs and ensure the absorption and bioavailability of topical pharmaceutical preparations of the compound of formula I, it is desirable to provide a topical pharmaceutical preparation (such as a gel and a topical solution) with stable properties and excellent effects.

Solutions to Solve Problems

In a first aspect, the present invention provides an amorphous substance of a compound of formula I, wherein the amorphous substance has an X-ray powder diffraction (XRPD) pattern that is free of sharp peaks, preferably has non-sharp peaks.

Further, the amorphous substance has about 10.0 wt % or less, preferably about 4.0 wt % or less of water.

Still further, the amorphous substance has a thermogravimetric analysis (TGA) pattern showing a weight loss of about 3.0% at 150±3° C.

Still further, the amorphous substance has a modulated differential scanning calorimetry (mDSC) pattern showing a glass transition temperature of 109.4±3° C.

In a second aspect, the present invention provides a method for preparing the amorphous substance of the compound of formula I, wherein the method is selected from a slow volatilization method, a slow cooling method, a gas-solid diffusion method, a gas-liquid diffusion method, a suspension stirring method and an anti-solvent addition method, preferably an anti-solvent addition method.

Further, the solvents used in the slow volatilization method are alcohols, ethers, esters, ketones, nitriles, halogenated hydrocarbons or aromatic hydrocarbons.

Further, the solvents used in the slow cooling method are at least one of alcohols, ethers, nitriles, esters, ketones, aliphatic hydrocarbons, aromatic hydrocarbons and water; the cooling rate of the slow cooling method is 0.1° C.-5° C./min.

Further, the solvents used in the gas-solid diffusion method are alcohols, ketones, esters, halogenated hydrocarbons or water.

Further, the solvents used in the gas-liquid diffusion method are ethers, ketones, nitriles or esters, and the anti-solvents used are aliphatic hydrocarbons or ethers.

Further, the solvents used in the suspension stirring method are water, aliphatic hydrocarbons, aromatic hydrocarbons, alcohols, ketones, esters, halogenated hydrocarbons, ethers, nitriles, dimethyl sulfoxide or amides.

Further, the good solvents used in the anti-solvent addition method are alcohols, ethers, ketones, esters, nitriles, amides, halogenated hydrocarbons or dimethyl sulfoxide, and the anti-solvents used are aliphatic hydrocarbons, ethers or water.

In a third aspect, the present invention provides a 1,5-naphthalene disulfonate of the compound of formula I.

Further, in the 1,5-naphthalene disulfonate of the compound of formula I, the molar ratio of the compound of formula I to 1,5-naphthalene disulfonic acid is about 1:0.2-1:5.0.

Preferably, the molar ratio of the compound of formula I to 1,5-naphthalene disulfonic acid is about 1:0.5-1:2.0.

More preferably, the molar ratio of the compound of formula I to 1,5-naphthalene disulfonic acid is about 1:1.0-1:1.5.

In a fourth aspect, the present invention provides an amorphous substance of the 1,5-naphthalene disulfonate of the compound of formula I, wherein the molar ratio of the compound of formula I to 1,5-naphthalene disulfonic acid is about 1:1.0, and the amorphous substance has an XRPD pattern that is free of sharp peaks, preferably has non-sharp peaks.

Further, the amorphous substance has about 10.0 wt % or less, preferably about 5.0 wt % or less of water.

Further, the amorphous substance has a solvent.

Preferably, the solvent is ethanol.

More preferably, the molar ratio of the compound of formula I to the ethanol is about 1:1.0.

Still further, the amorphous substance has a TGA pattern showing a weight loss of about 7.6% at 150±3° C.

Still further, the amorphous substance has an mDSC pattern showing a glass transition temperature of 178.4±3° C.

In a fifth aspect, the present invention provides a method for preparing the amorphous substance of the 1,5-naphthalene disulfonate of the compound of formula I, wherein the method comprises the steps of: stirring the compound of formula I and 1,5-naphthalene disulfonic acid in ethanol, and separating and drying the solid.

In a sixth aspect, the present invention provides a crystal of the 1,5-naphthalene disulfonate of the compound of formula I, wherein the molar ratio of the compound of formula I to 1,5-naphthalene disulfonic acid is about 1:1.5, and the crystal has a crystal form A, and has an XRPD pattern comprising peaks at 2θ values of: 12.6±0.2°, 16.8±0.2° and 25.3±0.2°.

Preferably, the crystal form A has an XRPD pattern comprising peaks at 2θ values of: 15.9±0.2°, 18.8±0.2°, 25.0±0.2° and 27.3±0.2°.

More preferably, the crystal form A has an XRPD pattern comprising peaks at 2θ values of: 23.4±0.2°, 23.8±0.2°, 29.6±0.2° and 38.0±0.2°.

Further, the crystal form A has about 10.0 wt % or less, preferably about 6.0 wt % or less of water.

Further, the crystal form A has a solvent.

Preferably, the solvent is methyl tert-butyl ether.

More preferably, the molar ratio of the compound of formula I to the methyl tert-butyl ether is about 1:1.0.

Still further, the crystal form A has a TGA pattern showing a weight loss of about 11.3% at 150±3° C.

Still further, the crystal form A has a DSC pattern showing heat absorption at 101±3° C. and 129±3° C.

In a seventh aspect, the present invention provides a method for preparing the crystal having the crystal form A of the 1,5-naphthalene disulfonate of the compound of formula I, wherein the method comprises the steps of: stirring the compound of formula I and 1,5-naphthalene disulfonic acid in methyl tert-butyl ether, and separating and drying the solid.

In an eighth aspect, the present invention provides a crystal of the 1,5-naphthalene disulfonate of the compound of formula I, wherein the molar ratio of the compound of formula I to 1,5-naphthalene disulfonic acid is about 1:1.1, and the crystal has a crystal form B, and has an XRPD pattern comprising peaks at 2θ values of: 11.6±0.2°, 17.0±0.2° and 23.0±0.2°.

Further, the crystal form B has about 15.0 wt % or less, preferably about 10.0 wt % or less of water.

Further, the crystal form B has a solvent.

Preferably, the solvent is methyl tert-butyl ether.

More preferably, the molar ratio of the compound of formula I to the methyl tert-butyl ether is about 1:0.5.

Still further, the crystal form B has a TGA pattern showing a weight loss of about 13.0% at 150±3° C.

Further, the crystal has a DSC pattern showing heat absoprtion at 98±3° C.

In a ninth aspect, the present invention provides a method for preparing the crystal having the crystal form B of the 1,5-naphthalene disulfonate of the compound of formula I, wherein the method comprises the steps of: stirring the compound of formula I and 1,5-naphthalene disulfonic acid in methyl tert-butyl ether (for example, stirring at room temperature for 1-5 days), performing cyclic heating and cooling at least once (the highest temperature in the cyclic heating and cooling is below the boiling point of the solvent, for example, 45° C.-55° C., and the lowest temperature is above 0° C.; the number of cycles is 2-5 times, such as 3 times and 4 times), and separating and drying the solid.

In a tenth aspect, the present invention provides a pharmaceutical composition comprising (preferably a preventively, alleviatedly and/or therapeutically effective amount of) at least one of an amorphous substance of the compound of formula I, a 1,5-naphthalene disulfonate of the compound of formula I, an amorphous substance of the 1,5-naphthalene disulfonate of the compound of formula I, a crystal having a crystal form A of the 1,5-naphthalene disulfonate of the compound of formula I, and a crystal having a crystal form B of the 1,5-naphthalene disulfonate of the compound of formula I, and an optional pharmaceutically acceptable excipient.

In an eleventh aspect, the present invention provides a pharmaceutical preparation (preferably a topical pharmaceutical preparation) comprising (preferably a preventively, alleviatedly and/or therapeutically effective amount of) at least one of an amorphous substance of the compound of formula I, a 1,5-naphthalene disulfonate of the compound of formula I, an amorphous substance of the 1,5-naphthalene disulfonate of the compound of formula I, a crystal having a crystal form A of the 1,5-naphthalene disulfonate of the compound of formula I, and a crystal having a crystal form B of the 1,5-naphthalene disulfonate of the compound of formula I (preferably an amorphous substance of the compound of formula I), and an optional pharmaceutically acceptable excipient (the excipient is preferably at least one of a solvent, a solubilizer or surfactant, a gel matrix material and a pH regulator).

In a twelfth aspect, the present invention provides the use of at least one of the amorphous substance of the compound of formula I, the 1,5-naphthalene disulfonate of the compound of formula I, the amorphous substance of the 1,5-naphthalene disulfonate of the compound of formula I, the crystal having the crystal form A of the 1,5-naphthalene disulfonate of the compound of formula I, and the crystal having the crystal form B of the 1,5-naphthalene disulfonate of the compound of formula I, or a pharmaceutical composition or pharmaceutical preparation (preferably a topical pharmaceutical preparation) comprising same in the preparation of a drug.

Further, the drug is used for prevention, alleviation and/or therapy of at least one of acne, hirsutism, sebaceous gland enlargement, alopecia, asthma, multiple sclerosis, cancer, Kennedy's disease, ciliopathy, cleft palate, diabetes, heart disease, high blood pressure, inflammatory bowel disease, mental retardation, mood disorder, obesity, refractive errors, infertility, Angelman syndrome, Canavan disease, coeliac disease, Charcot-Marie-Tooth disease, cystic fibrosis, Duchenne muscular dystrophy, hemochromatosis, hemophilia, Klinefelter's syndrome, phenylketonuria, polycystic kidney disease, Prader-Willi syndrome, sickle cell disease, Tay-Sachs disease and Turner syndrome.

Still further, the cancer includes squamous cell carcinoma, basal cell carcinoma and adenocarcinoma; leukemia; benign and malignant lymphomas, especially Burkitt's lymphoma and non-Hodgkin's lymphoma; benign and malignant melanomas; myeloproliferative diseases; sarcoma, including Ewing's sarcoma, hemangioendothelioma, Kaposi's sarcoma, liposarcoma, myosarcoma, peripheral neuroepithelioma, synovial sarcoma, glioma, astrocytoma, oligodendroglioma, ependymoma, glioblastoma, neuroblastoma, ganglioglioma, medulloblastoma, pinealocytoma, meningioma, meningeal sarcoma, neurofibroma and Schwannomas; head and neck cancer, breast cancer, bladder cancer, prostate cancer, cervical cancer, uterine cancer, lung cancer, ovarian cancer, testicular cancer, thyroid cancer, esophageal cancer, pancreatic cancer, gastric cancer, liver cancer, kidney cancer and colon cancer; carcinosarcoma, Hodgkin's disease, Wilms tumor or teratocarcinoma.

Effects of the Invention (1) The present invention provides an amorphous substance of a compound of formula I, and an amorphous substance and two crystals of a 1,5-naphthalene disulfonate of the compound of formula I. Experimental results show that the amorphous substance of the compound of formula I has excellent stability, and in long-term stability, accelerated stability and high-temperature stability experiments, the amorphous substance of the compound of formula I of the present invention exhibits excellent stability and is suitable for pharmaceutical studies.

(2) In the salt formation study, the applicant is surprised to find that only 1,5-naphthalene disulfonic acid is capable of obtaining a solid form of salt with the compound of formula I, so that impurities can be removed from a free alkali by salt formation to achieve the purpose of purification.

(3) In the present invention, it is also surprised to find that after administration via skin application, the amorphous substance of the compound of formula I can enter sebaceous glands but cannot enter blood; In other words, the pharmaceutical preparation (especially a topical drug) made from the amorphous substance can effectively avoid systemic exposure to the drug to reduce or avoid side effects while achieving efficacy; for example, administration of the pharmaceutical preparation to the skin or scalp site in the form of a gel or a topical solution can be used for therapy of acne or alopecia to reduce or avoid side effects caused by oral administration of androgen signaling pathway inhibitors.

(4) In the present invention, corresponding optimization on the solvent system in the pharmaceutical preparation (especially a topical drug) comprising the amorphous substance of the compound of formula I is also made; when a ternary solvent compounding system involving ethanol is used, not only the problem of poor solubility of the amorphous substance of the compound of formula I is solved, but also the content of ethanol can be controlled to 50% v/v or less, avoiding skin irritation that may be caused by excessive ethanol content (for example, greater than 50% v/v), which meets the requirements of Handbook of Pharmaceutical Excipients (8th edition, page 358).

(5) In the present invention, a surfactant is added when the topical solution or the gel of the compound of formula I is developed, solving the problem of poor physical stability of the topical solution or the gel.

DETAILED DESCRIPTION OF EMBODIMENTS

Figure 1:
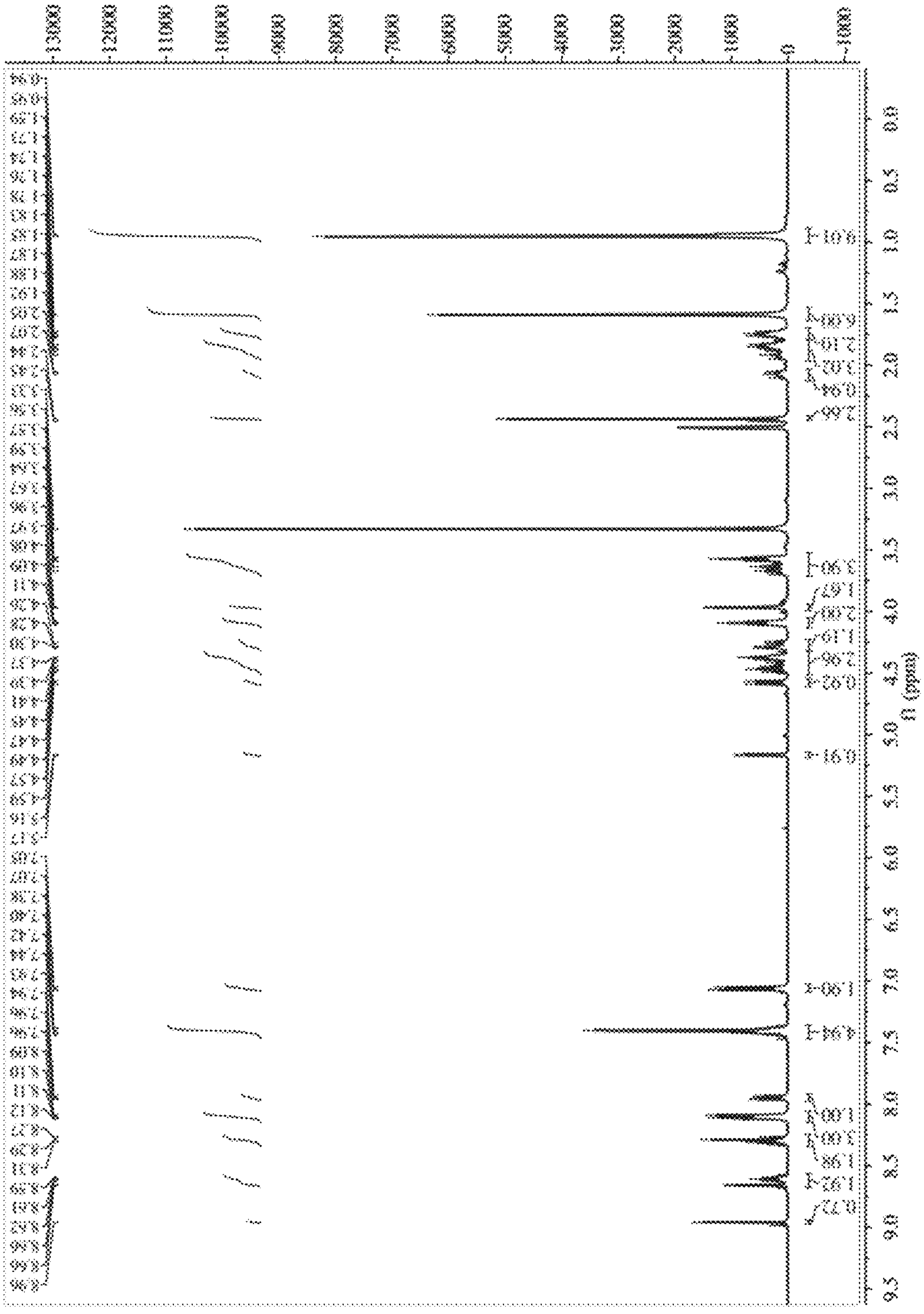
FIG. 1 shows a $^{1}$H-NMR pattern of the compound of formula I.

Unless otherwise specified, all scientific and technical terms used herein have the meanings commonly understood by a person skilled in the art.

Unless otherwise specified, words in the singular form appearing herein, such as "a", "an" and "the", covers their corresponding plural referents, unless the context clearly indicates otherwise. For example, when referring to "a" crystal form, crystal or polymorph, different crystal form(s), crystal(s) or polymorph(s) are covered, and when referring to "the" method, equivalent steps and methods known to one of ordinary skill in the art are covered.

For the crystal forms herein, only the characteristic peaks (i.e., the most characteristic, significant, unique and/or repeatable diffraction peaks) in the XRPD pattern are summarized, while other peaks can be obtained from the patterns by conventional methods. The above-mentioned characteristic peaks can be repeated within an error limit (error range is ±0.2°.

Unless otherwise specified, the term "comprise" and variations, such as "contain" and "include", appearing herein means that a set covers not only explicitly disclosed integer(s), step(s) or combinations thereof, but also does not exclude any other integers, steps or combinations thereof. Furthermore, in certain cases, the term "comprise" appearing herein can be replaced with the term "contain", "include" or "have".

Unless otherwise specified, the term "effective amount" appearing herein means an amount of a pharmacologically active ingredient that is sufficient to affect a disease or a symptom after the pharmacologically active ingredient has been administered to an individual/subject/patient for the prevention, alleviation and/or therapy of the disease or disorder. The "effective amount" can vary depending on factors such as the pharmacologically active ingredient, the symptom or severity of the disease or disorder, and the personal information (for example, age, sex and weight, etc.) of the individual/subject/patient.

Unless otherwise specified, the pharmaceutical composition comprising the amorphous substance and/or the crystal of the present invention can be administered to an individual/subject/patient in need thereof via routes such as oral administration, inhalation administration, rectum administration, parenteral administration or topical administration. For oral administration, the pharmaceutical composition can be a solid preparation (for example, a tablet, a powder, a granule and a capsule, etc.), a semi-solid preparation (for example, a gel, an ointment and a cream, etc.) and a liquid preparation (for example, a water-based or oil-based suspension or other liquid preparation, such as a topical solution, a syrup and a solution, etc.). For parenteral administration, the pharmaceutical composition can be a solution, a suspension, a freeze-dried powder, etc. For topical administration, the pharmaceutical composition can be a gel, a topical solution, etc. The pharmaceutical composition can be a single unit having an accurate dose. In addition, the pharmaceutical composition can further comprise additional pharmacologically active ingredients.

For example, corresponding gels or topical solutions can be prepared using the amorphous substance of the compound of formula I of the present invention. The components of the gel can comprise the amorphous substance of the compound of formula I, a solvent, a solubilizer or surfactant, a gel matrix material and a pH regulator, and the weight percentage of the amorphous substance of the compound of formula I in the gel can be 0.1%-10.0% (for example, 0.1%-8.0%, 0.1%-5.0%, 0.1%-3.0%, 0.1%-2.0%, 0.1%-1.0%, 0.2%-10.0%, 0.2%-8.0%, 0.2%-5.0%, 0.2%-3.0%, 0.2%-2.0%, 0.2%-1.0%, 0.3%-10.0%, 0.3%-8.0%, 0.3%-5.0%, 0.3%-3.0%, 0.3%-2.0%, 0.3%-1.0%, 0.5%-10.0%, 0.5%-8.0%, 0.5%-5.0%, 0.5%-3.0%, 0.5%-2.0%, 0.5%-1.0%, 0.6%, 0.7%, 0.8%, 0.9%, 1.0%, etc.). The components of the topical solution can comprise the amorphous substance of the compound of formula I, a solvent, and a solubilizer or surfactant, and the weight percentage of the amorphous substance of the compound of formula I in the topical solution can be 0.1%-10.0% (for example, 0.1%-8.0%, 0.1%-5.0%, 0.1%-3.0%, 0.1%-2.0%, 0.1%-1.0%, 0.2%-10.0%, 0.2%-8.0%, 0.2%-5.0%, 0.2%-3.0%, 0.2%-2.0%, 0.2%-1.0%, 0.3%-10.0%, 0.3%-8.0%, 0.3%-5.0%, 0.3%-3.0%, 0.3%-2.0%, 0.3%-1.0%, 0.5%-10.0%, 0.5%-8.0%, 0.5%-5.0%, 0.5%-3.0%, 0.5%-2.0%, 0.5%-1.0%, 0.6%, 0.7%, 0.8%, 0.9%, 1.0%, etc.).

In the above-mentioned gel or topical solution, the solvent can be a combination of any one or more of alcohol solvents with water. Non-limiting examples of the alcohol solvents include (but are not limited to) (dehydrated) alcohol, propylene glycol, polyethylene glycol, diethylene glycol monoethyl ether, glycerin, isopropyl alcohol, benzyl alcohol, lanolin alcohol, butanediol, etc., preferably one or more of (dehydrated) ethanol, propylene glycol and glycerin.

In the above-mentioned gel or topical solution, the solubilizer or surfactant can be any one or more of poloxamer 188, polyoxyethylene 40 hydrogenated castor oil (RH40), polyoxyethylene 35 castor oil, span 40, glyceryl mono- and distearate, polyethylene glycol (35) stearate, polyglyceryl-3 distearate and Tween 80, preferably Tween 80. The weight percentage of the solubilizer or surfactant in the gel or topical solution can be 1%-15% (for example, 1%-12%, 1%-10%, 1%-8%, 1%-5%, 2%-15%, 2%-12%, 2%-10%, 2%-8%, 2%-5%, 3%-10%, 3%-8%, 3%-7%, 3%-6%, 3%-5%, 4%-10%, 4%-8%, 4%-7%, 4%-6%, 4%-5%, 5%, etc.).

In the above-mentioned gel, the gel matrix material can be any one or more of sodium carboxymethyl cellulose, methyl cellulose, hydroxypropyl methyl cellulose, hydroxypropyl cellulose, poloxamer 407 and carbomer, preferably carbomer or sodium carboxymethyl cellulose. The amount of the gel matrix material in the gel can be 0.01%-5.0% (for example, 0.02%-5.0%, 0.03%-5.0%, 0.05%-5.0%, 0.08%-5.0%, 0.1%-5.0%, 0.1%-4.0%, 0.1%-3.0%, 0.1%-2.0%, 0.1%-1.0%, 0.2%-5.0%, 0.2%-4.0%, 0.2%-3.0%, 0.2%-2.0%, 0.2%-1.0%, 0.3%-3.0%, 0.3%-2.0%, 0.3%-1.0%, 0.4%-3.0%, 0.4%-2.0%, 0.4%-1.0%, 0.5%, 0.6%, 0.7%, 0.8%, 0.9%, 1.0%, etc.).

In the above-mentioned gel, the pH regulator can be any one or more of tromethamine, sodium hydroxide, sodium bicarbonate, ethylenediamine, ethanolamine, ammonia water and triethanolamine, preferably triethanolamine, for adjusting the pH value of the gel to 5-8, preferably 5-7. In the preparation of the above-mentioned gel, the pH regulator and the gel matrix material need to be used together in order to control the viscosity of the gel.

Amorphous Substance of Free Alkali and Preparation Method Thereof

Figure 2:
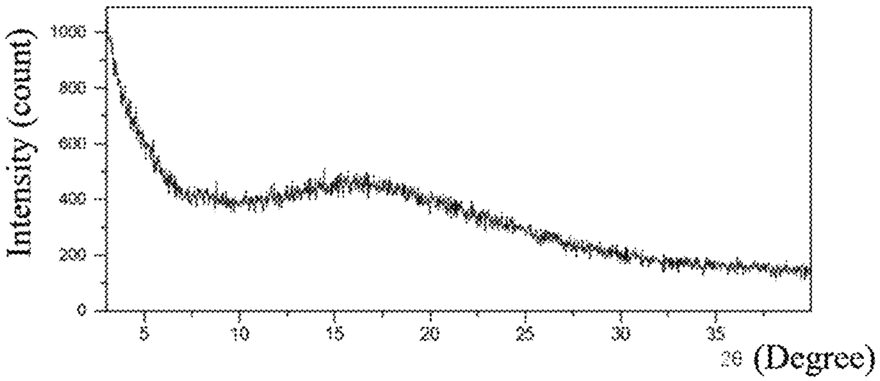
FIG. 2 shows an XRPD pattern of the amorphous substance of the compound of formula I.
Figure 3:
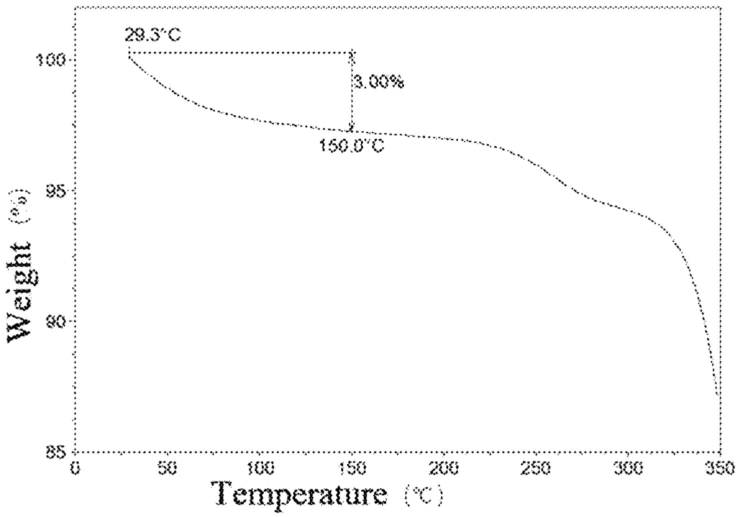
FIG. 3 shows a TGA pattern of the amorphous substance of the compound of formula I.
Figure 4:
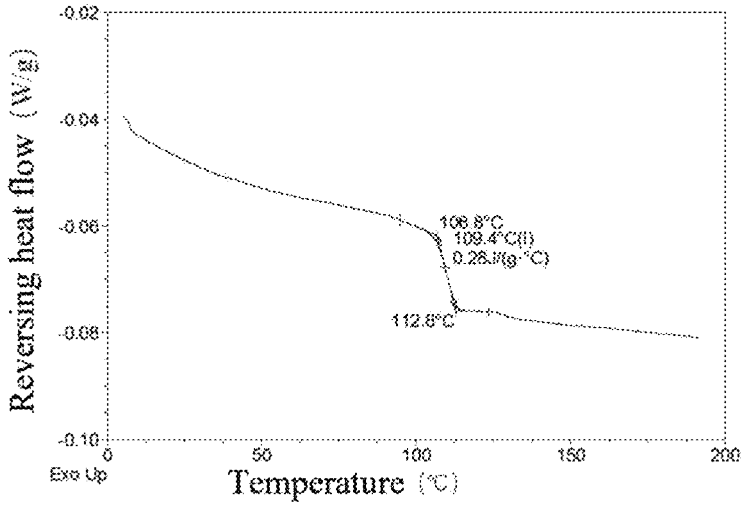
FIG. 4 shows an mDSC pattern of the amorphous substance of the compound of formula I.
Figure 5:
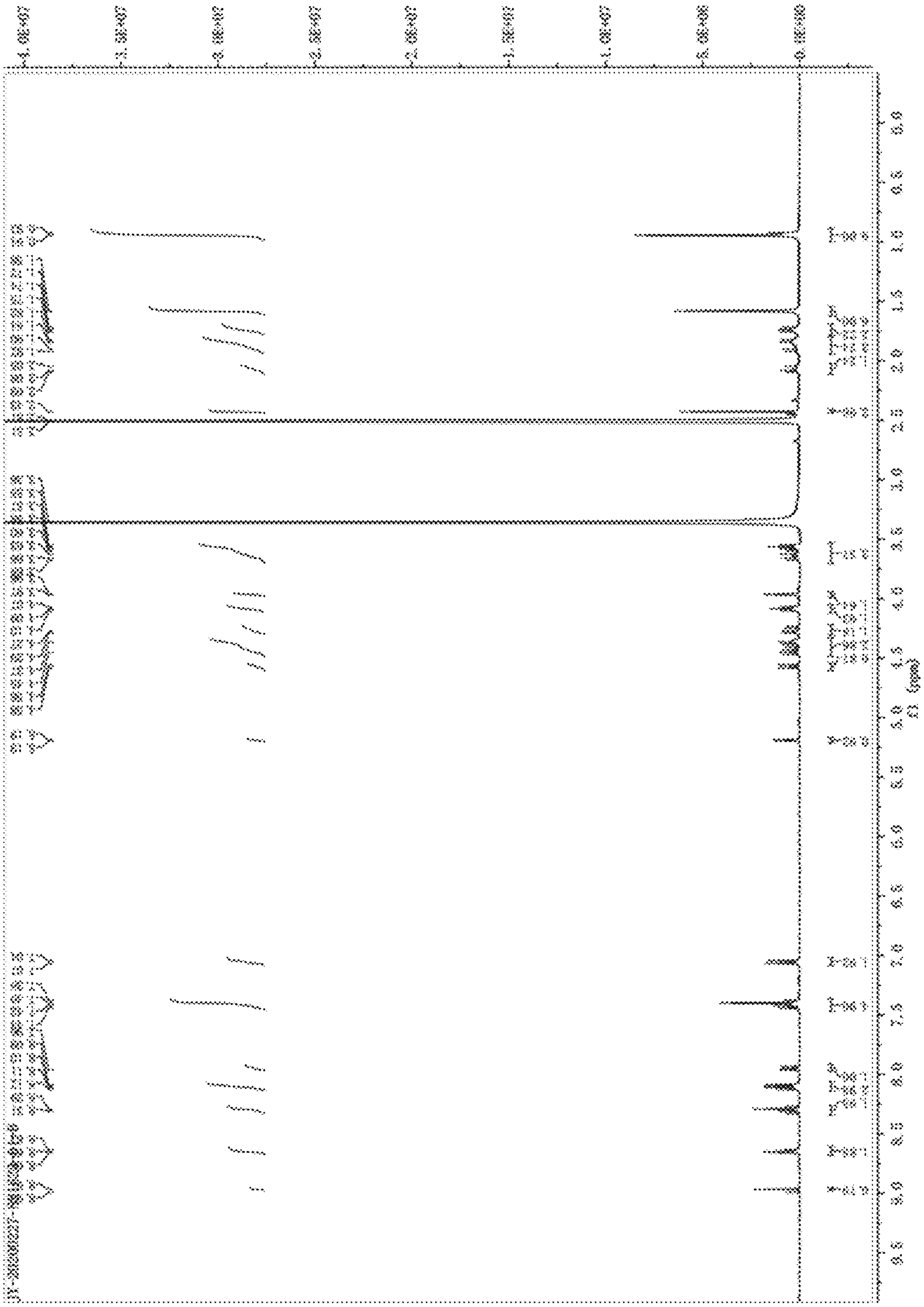
FIG. 5 shows a H-NMR pattern of the amorphous substance of the compound of formula I.

The present invention provides an amorphous substance of the compound of formula I, having a measured XRPD pattern substantially consistent with FIG. 2, a measured TGA pattern substantially consistent with FIG. 3, a measured mDSC pattern substantially consistent with FIG. 4, and a measured $^1$H-NMR pattern substantially consistent with FIG. 5.

By the XRPD pattern, it can be found that the amorphous substance has the XRPD pattern that is free of sharp peaks, but has non-sharp peaks, particularly has a non-sharp peak in a 2θ value range of 5°-25°, for example, in a 2θ value range of about 10°-20°, particularly at a 2θ value of about 16°.

In the present invention, the amorphous substance can have water adsorbed from the environment, and the water content of the amorphous substance can be, in percentage by weight (wt %), about 10.0 wt % or less, preferably about 4.0 wt % or less, for example, about 3.0 wt %.

By the TGA pattern, it can be found that the amorphous substance shows a weight loss of about 3.0% at 150±3° C.

By the mDSC pattern, it can be found that the amorphous substance has a glass transition temperature of 109.4±3° C.

In the present invention, the amorphous substance can be prepared by a slow volatilization method, a slow cooling method, a gas-solid diffusion method, a gas-liquid diffusion method, a suspension stirring method or an anti-solvent addition method.

In one embodiment, the amorphous substance can be prepared by a slow volatilization method. The method comprises dissolving the compound of formula I in a solvent and performing slow volatilization at atmospheric pressure. Solvents suitable for the method can be, for example, alcohols (for example, methanol, ethanol, isopropyl alcohol, etc., preferably methanol), ethers (for example, tetrahydrofuran, 2-methyltetrahydrofuran, 1,4-dioxane, etc.), esters (for example, ethyl acetate, isopropyl acetate, etc., preferably isopropyl acetate), ketones (for example, acetone, methyl isobutyl ketone, etc., preferably methyl isobutyl ketone), nitriles (such as acetonitrile), halogenated hydrocarbons (such as chloroform), or aromatic hydrocarbons (such as toluene).

In one embodiment, the amorphous substance can be prepared by a slow cooling method. The method comprises dissolving the compound of formula I in a solvent at a temperature below the boiling point (for example, 50° C.) and then performing slow cooling at a rate of 0.1° C.-5° C./min (for example, 0.1° C./min, until 5° C.). Solvents suitable for the method can be, for example, at least one of alcohols (for example, methanol, ethanol, etc.), ethers (such as tetrahydrofuran), nitriles (such as acetonitrile), esters (such as isopropyl acetate), ketones (such as methyl isobutyl ketone), aliphatic hydrocarbons (for example, n-cyclohexane, n-heptane, etc.), aromatic hydrocarbons (such as toluene) and water. When the method uses a mixed solvent formed from two or more solvents, the mixed solvent can be, for example, ethanol/n-heptane (such as at a volume ratio of 1/4), acetone/n-heptane (such as at a volume ratio of 1/4), ethyl acetate/n-heptane (such as at a volume ratio of 1/4), isopropyl alcohol/cyclohexane (such as at a volume ratio of 1/9), acetone/cyclohexane (such as at a volume ratio of 1/9), methanol/water (such as at a volume ratio of 1/4), ethanol/water (such as at a volume ratio of 1/4), acetonitrile/water (such as at a volume ratio of 1/4), tetrahydrofuran/water (such as at a volume ratio 1/4), tetrahydrofuran/n-heptane (such as at a volume ratio of 1/4), isopropyl acetate/n-heptane (such as at a volume ratio of 1/2), or methyl isobutyl ketone/cyclohexane (such as at a volume ratio of 1/4).

In one embodiment, the amorphous substance can be prepared by a gas-solid diffusion method. The method comprises placing the solid form of the compound of formula I in a gas phase atmosphere formed by solvent volatilization, allowing the solid-state compound of formula I to interact with the gaseous-state solvent. Solvents suitable for the method can be, for example, alcohols (for example, ethanol, isopropyl alcohol, etc.), ketones (such as acetone), esters (such as ethyl acetate), halogenated hydrocarbons (such as dichloroethane), or water.

In one embodiment, the amorphous substance can be prepared by a gas-liquid diffusion method. The method comprises dissolving the compound of formula I in a good solvent, and then placing the resulting product in a gas phase atmosphere formed by anti-solvent volatilization, allowing the liquid-state compound of formula I to interact with the gaseous-state anti-solvent. Good solvents suitable for the method can be, for example, ethers (such as 1,4-dioxane), ketones (such as methyl isobutyl ketone), nitriles (such as acetonitrile) or esters (such as ethyl acetate), and anti-solvents can be, for example, aliphatic hydrocarbons (for example, n-heptane, cyclohexane, etc.) or ethers (such as methyl tert-butyl ether). Suitable good solvent/anti-solvent combinations can be, for example, 1,4-dioxane/n-heptane, methyl isobutyl ketone/cyclohexane, ethyl acetate/methyl tert-butyl ether, or acetonitrile/methyl tert-butyl ether.

In one embodiment, the amorphous substance can be prepared by a suspension stirring method (also known as a beating method). The method comprises placing the solid form of the compound of formula I in a solvent and stirring the resulting suspension, preferably at 5° C.-50° C. in a cyclic heating and cooling manner, more preferably at room temperature. Solvents suitable for the method can be, for example, water, aliphatic hydrocarbons (for example, cyclohexane, n-heptane, etc.), aromatic hydrocarbons (such as toluene), alcohols (such as methanol, ethanol and isopropyl alcohol), ketones (such as methyl isobutyl ketone), esters (for example, ethyl acetate, isopropyl acetate, etc.), halogenated hydrocarbons (for example, dichloromethane, chloroform, etc.), ethers (for example, tetrahydrofuran, methyl tert-butyl ether, 1,4-dioxane, etc.), nitriles (such as acetonitrile), dimethyl sulfoxide, or amides (for example, N,N-dimethylacetamide, N-methylpyrrolidone,etc.). When the method uses a mixed solvent formed from two or more solvents, the mixed solvent can be, for example, 1,4-dioxane/water (such as at a volume ratio of 1:4), methanol/water (such as at a volume ratio of 1:4), dimethyl sulfoxide/water (such as at a volume ratio of 1:4), ethyl acetate/cyclohexane (such as at a volume ratio of 1:9), tetrahydrofuran/cyclohexane (such as at a volume ratio of 1:9), isopropyl acetate/n-heptane (such as at a volume ratio of 1:9), or dichloromethane/n-heptane (such as at a volume ratio of 1:9).

In one embodiment, the amorphous substance can be prepared by an anti-solvent addition method. The method comprises dissolving the compound of formula I in a good solvent and then adding an anti-solvent. The solubility of the compound of formula I in the good solvent is greater than that in the anti-solvent, and the addition of the anti-solvent to the good solvent can make the compound of formula I dissolved in the good solvent to precipitate out as a solid, so as to obtain the amorphous substance. Good solvents suitable for the method can be, for example, alcohols (for example, methanol, ethanol, isopropyl alcohol, etc.), ethers (for example, tetrahydrofuran, 1,4-dioxane, etc.), ketones (for example, acetone, methyl isobutyl ketone, etc.), esters (for example, ethyl acetate and isopropyl acetate, etc.), nitriles (such as acetonitrile), amides (for example, N,N-dimethylacetamide, N-methylpyrrolidone, etc.), halogenated hydrocarbons (such as chloroform) or dimethyl sulfoxide, and anti-solvents can be, for example, aliphatic hydrocarbons (for example, cyclohexane, n-heptane, etc.), ethers (such as methyl tert-butyl ether) or water. Suitable good solvent/anti-solvent combinations can be, for example, acetone/n-heptane, methanol/water, isopropyl alcohol/water, N,N-dimethylacetamide/water, or dimethyl sulfoxide/water.

Pharmaceutically Acceptable Salt, Amorphous Substance of Pharmaceutically Acceptable Salt, and Preparation Method Therefor The present invention provides a 1,5-naphthalene disulfonate of the compound of formula I, wherein the compound of formula I as an alkali and 1,5-naphthalene disulfonic acid as an acid can be prepared into a salt at a particular molar ratio.

In one embodiment of the present invention, the molar ratio of the compound of formula I to the 1,5-naphthalene disulfonic acid in the pharmaceutically acceptable salt can be about 1:0.2-1:5.0, such as 1:0.2, 1:0.3, 1:0.4, 1:0.5, 1:0.6, 1:0.7, 1:0.8, 1:0.9, 1:1.0, 1:1.1, 1:1.2, 1:1.3, 1:1.4, 1:1.5, 1:2.0, 1:2.5, 1:3.0, 1:4.0 or 1:5.0.

In another embodiment of the present invention, the molar ratio of the compound of formula I to the 1,5-naphthalene disulfonic acid in the pharmaceutically acceptable salt can be about 1:0.5-1:2.0, such as 1:0.5, 1:0.6, 1:0.7, 1:0.8, 1:0.9, 1:1.0, 1:1.1, 1:1.2, 1:1.3, 1:1.4, 1:1.5 or 1:2.0.

In still another embodiment of the present invention, the molar ratio of the compound of formula I to the 1,5-naphthalene disulfonic acid in the pharmaceutically acceptable salt can be about 1:1.0-1:1.5, such as 1:1.0, 1:1.1, 1:1.2, 1:1.3, 1:1.4 or 1:1.5.

Figure 6:
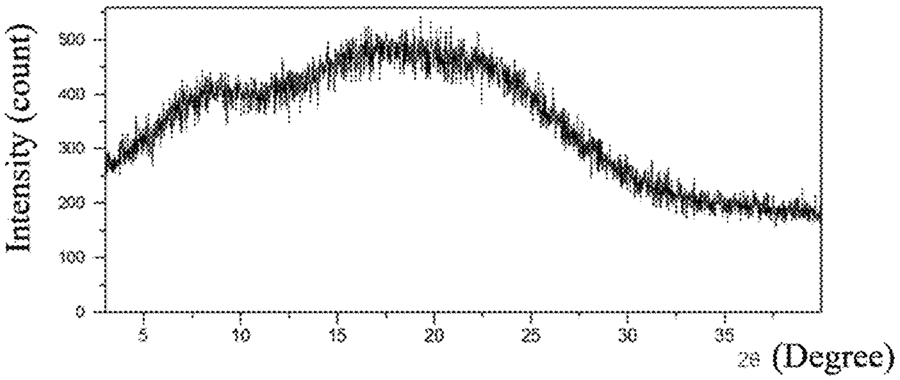
FIG. 6 shows an XRPD pattern of the amorphous substance of the 1,5-naphthalene disulfonate of the compound of formula I.
Figure 7:
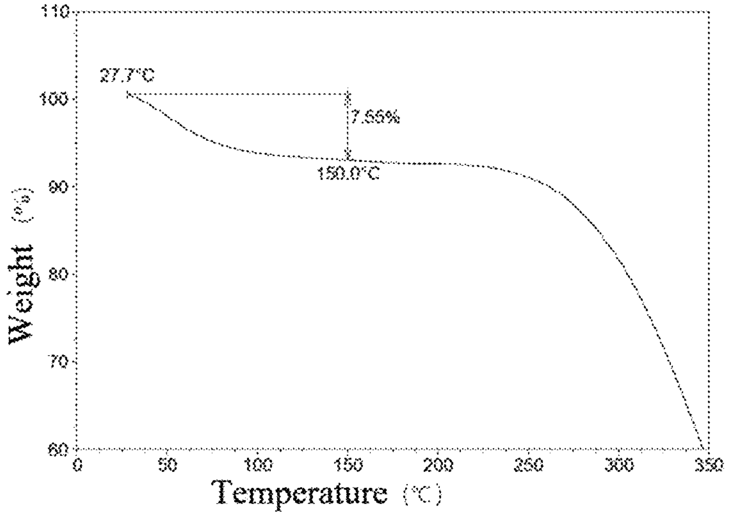
FIG. 7 shows a TGA pattern of the amorphous substance of the 1,5-naphthalene disulfonate of the compound of formula I.
Figure 8:
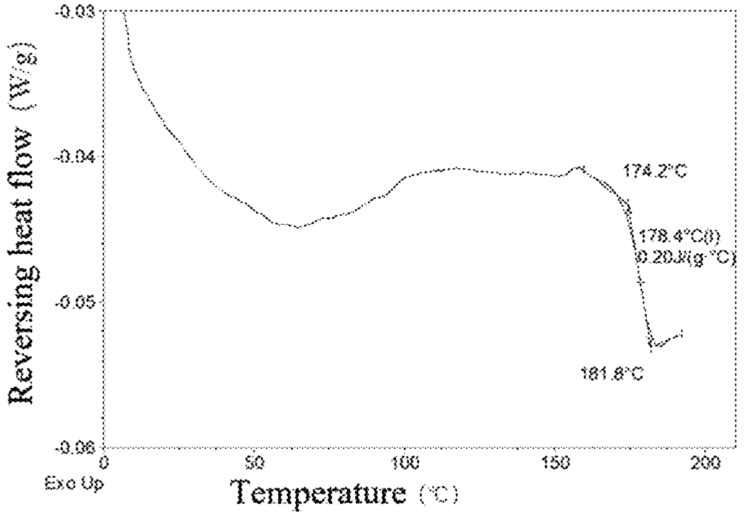
FIG. 8 shows an mDSC pattern of the amorphous substance of the 1,5-naphthalene disulfonate of the compound of formula I.
Figure 9:
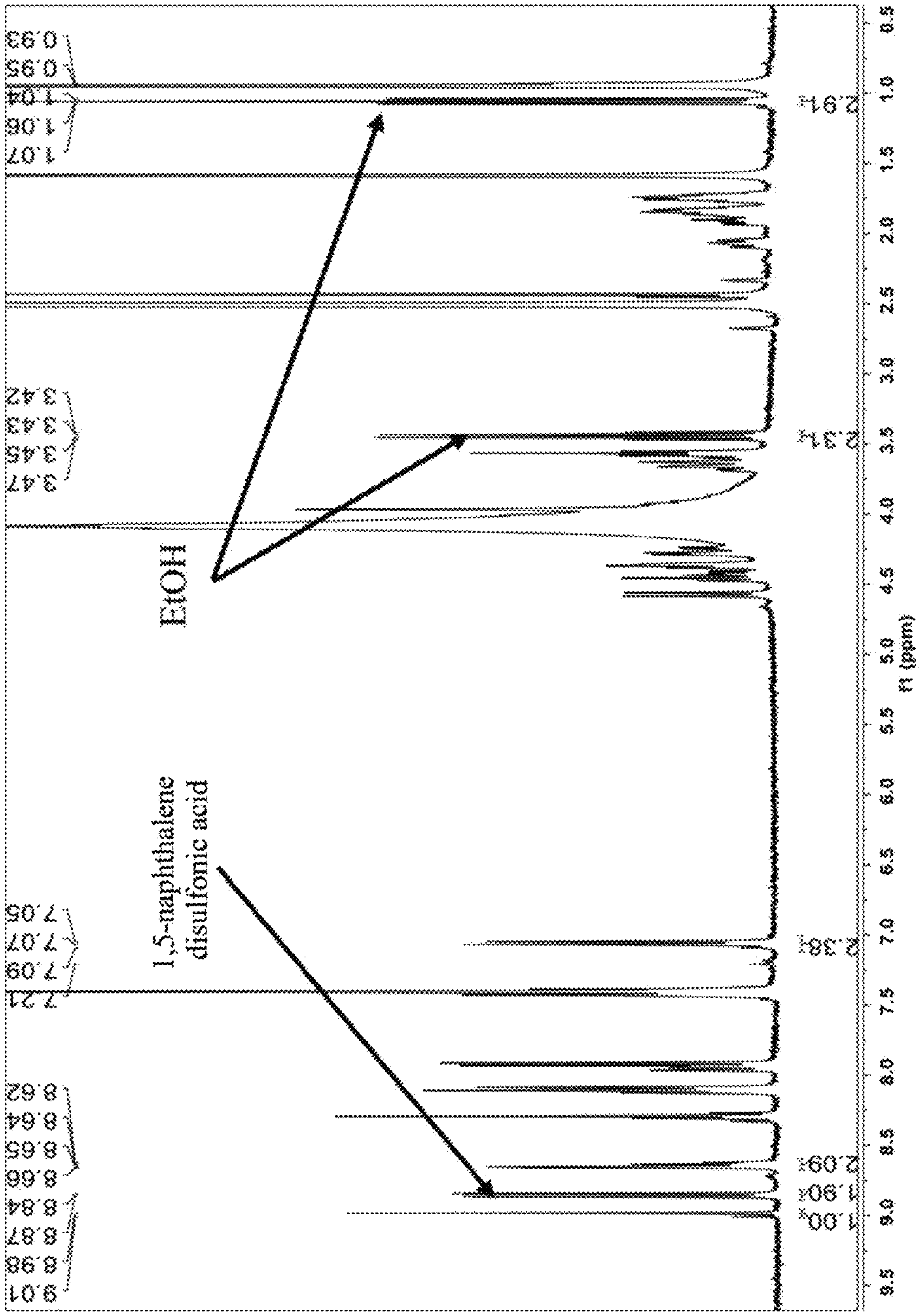
FIG. 9 shows a $^1$H-NMR pattern of the amorphous substance of the 1,5-naphthalene disulfonate of the compound of formula I.

The present invention provides an amorphous substance of the 1,5-naphthalene disulfonate of the compound of formula I, having a measured XRPD pattern substantially consistent with FIG. 6, a measured TGA pattern substantially consistent with FIG. 7, a measured mDSC pattern substantially consistent with FIG. 8, and a measured $^1$H-NMR pattern substantially consistent with FIG. 9.

By the XRPD pattern, it can be found that the amorphous substance has the XRPD pattern that is free of sharp peaks, but has non-sharp peaks, particularly has two non-sharp peaks in a 2θ value range of 5°-25°, for example, in a 2θ value range of about 7°-22°, particularly at 2θ values of about 7° and 16°, respectively.

In the present invention, the amorphous substance can have water adsorbed from the environment, and the water content of the amorphous substance can be, in percentage by weight, about 10.0 wt % or less, preferably about 5.0 wt % or less, for example, 4.3 wt %.

In the present invention, the amorphous substance can have residual solvent.

The amorphous substance can have, in percentage by weight, about 10.0 wt % or less, preferably about 5.0 wt % or less, for example, 3.3 wt %, of the residual solvent.

In one embodiment of the present invention, the solvent in the amorphous substance can be ethanol (or referred to EtOH).

In one embodiment of the present invention, the molar ratio of the compound of formula I to the ethanol in the amorphous substance can be about 1:0.5 to 1.5, such as 1:0.5, 1:0.6, 1:0.7, 1:0.8, 1:0.9, 1:1.0, 1:1.1, 1:1.2, 1:1.3, 1:1.4 or 1:1.5.

In one preferred embodiment of the present invention, the molar ratio of the compound of formula I to the ethanol in the amorphous substance of the above-mentioned pharmaceutically acceptable salt can be about 1:1.0.

By the TGA pattern, it can be found that the amorphous substance shows a weight loss of about 7.6% at 150±3° C.

By the mDSC pattern, it can be found that the amorphous substance has a glass transition temperature of 178.4±3° C.

In one embodiment of the present invention, the molar ratio of the compound of formula I to the 1,5-naphthalene disulfonic acid in the amorphous substance can be about 1:0.5 to 1.5, such as 1:0.5, 1:0.6, 1:0.7, 1:0.8, 1:0.9, 1:1.0, 1:1.1, 1:1.2, 1:1.3, 1:1.4 or 1:1.5.

In one preferred embodiment of the present invention, the molar ratio of the compound of formula I to the 1,5-naphthalene disulfonic acid in the amorphous substance can be about 1:1.0.

In the present invention, the amorphous substance can be prepared by the steps of: stirring the compound of formula I and 1,5-naphthalene disulfonic acid in ethanol, and separating and drying the solid.

Crystal of Pharmaceutically Acceptable Salt and Preparation Method Therefor

Figure 10:
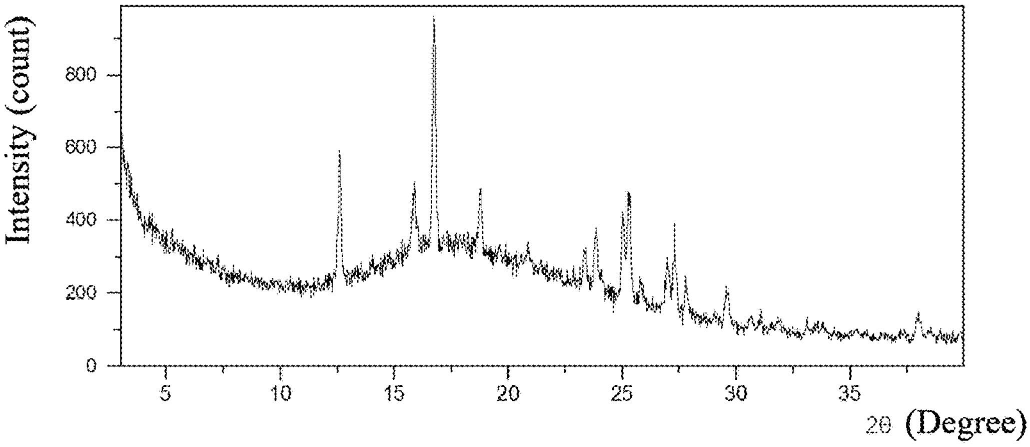
FIG. 10 shows an XRPD pattern of the crystal form A of the 1,5-naphthalene disulfonate of the compound of formula I.
Figure 11:
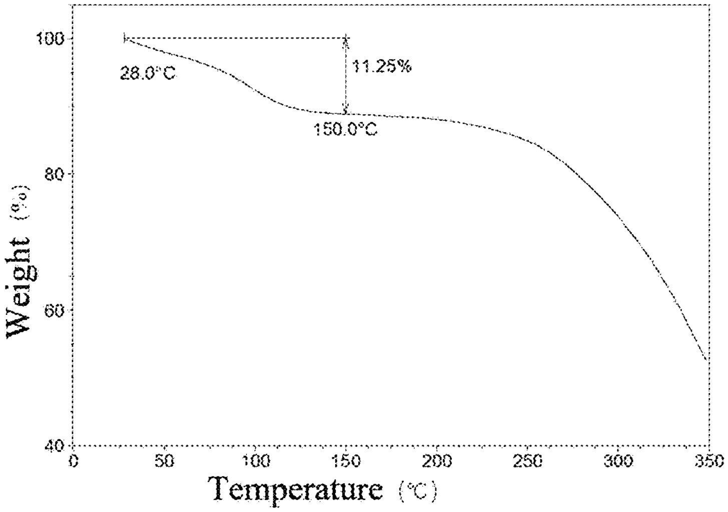
FIG. 11 shows a TGA pattern of the crystal form A of the 1,5-naphthalene disulfonate of the compound of formula I.
Figure 12:
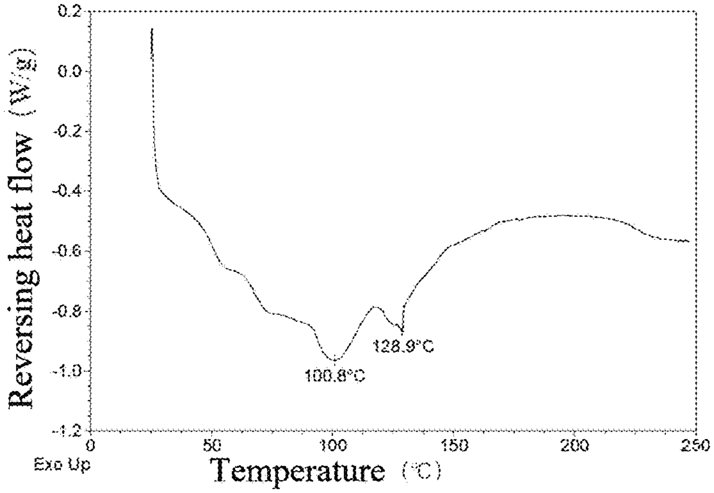
FIG. 12 shows a DSC pattern of the crystal form A of the 1,5-naphthalene disulfonate of the compound of formula I.
Figure 13:
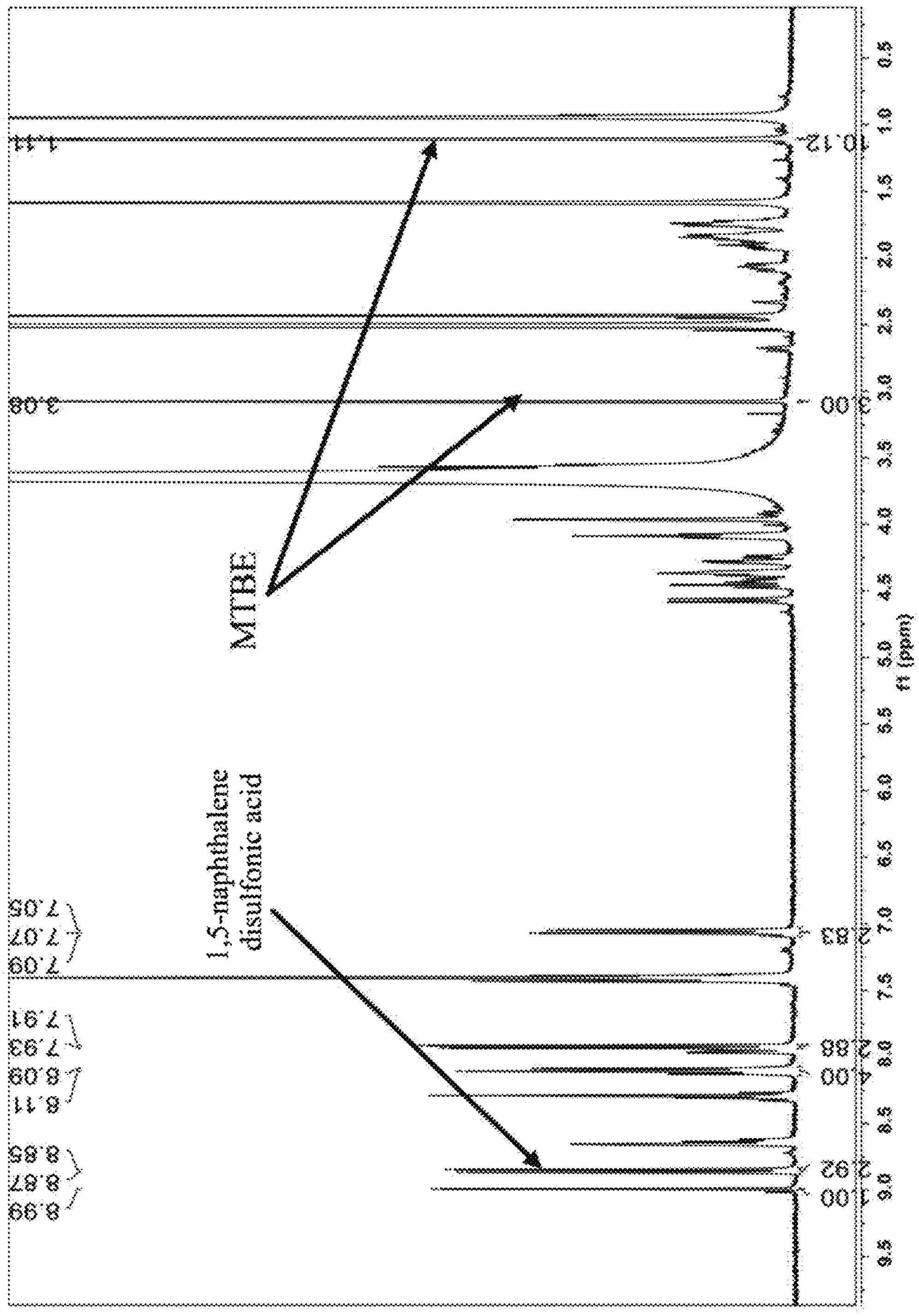
FIG. 13 shows a $^1$H-NMR pattern of the crystal form A of the 1,5-naphthalene disulfonate of the compound of formula I.

The present invention provides a first crystal of the 1,5-naphthalene disulfonate of the compound of formula I, having a crystal form A and having a measured XRPD pattern substantially consistent with FIG. 10, a measured TGA pattern substantially consistent with FIG. 11, a measured DSC pattern substantially consistent with FIG. 12, and a measured $^1$H-NMR pattern substantially consistent with FIG. 13.

By the XRPD pattern, it can be found that crystal form A has diffraction peaks with high relative-intensity at 2θ values of: 12.6±0.2°, 16.8±0.2° and 25.3±0.2°. In addition to this, crystal form A also has diffraction peaks with medium relative-intensity at 2θ values of: 15.9±0.2°, 18.8±0.2°, 25.0±0.2° and 27.3±0.2°. In addition to this, crystal form A also has diffraction peaks with low relative-intensity at 2° values of: 23.4±0.2°, 23.8±0.2°, 29.6±0.2° and 38.0±0.2°.

In the present invention, the crystal can have water adsorbed from the environment, and the water content of the amorphous substance can be, in percentage by weight, about 10.0 wt % or less, preferably about 6.0 wt % or less, for example, about 5.7 wt %.

In the present invention, the crystal can have residual solvent.

The crystal can have, in percentage by weight, about 10.0 wt % or less, preferably about 6.0 wt % or less, for example, 5.6 wt %, of the residual solvent.

In one embodiment of the present invention, the solvent in the crystal can be methyl tert-butyl ether (or referred to MTBE).

In one embodiment of the present invention, the molar ratio of the compound of formula I to the methyl tert-butyl ether in the crystal can be about 1:0.5 to 1.5, such as 1:0.5, 1:0.6, 1:0.7, 1:0.8, 1:0.9, 1:1.0, 1:1.1, 1:1.2, 1:1.3, 1:1.4 or 1:1.5.

In one preferred embodiment of the present invention, the molar ratio of the compound of formula I to the methyl tert-butyl ether in the crystal can be about 1:1.0.

By the TGA pattern, it can be found that the crystal shows a weight loss of about 11.3% at 150±3° C.

By the DSC pattern, it can be found that the crystal shows heat absorption at 101±3° C. and 129±3° C.

In one embodiment of the present invention, the molar ratio of the compound of formula I to the 1,5-naphthalene disulfonic acid in the crystal can be about 1:1.0 to 2.0, such as 1:1.0, 1:1.1, 1:1.2, 1:1.3, 1:1.4, 1:1.5, 1:1.6, 1:1.7, 1:1.8, 1:1.9 or 1:2.0.

In one preferred embodiment of the present invention, the molar ratio of the compound of formula I to the 1,5-naphthalene disulfonic acid in the crystal can be about 1:1.5.

In the present invention, the crystal can be prepared by the steps of: stirring the compound of formula I and 1,5-naphthalene disulfonic acid in methyl tert-butyl ether, and separating and drying the solid.

Figure 14:
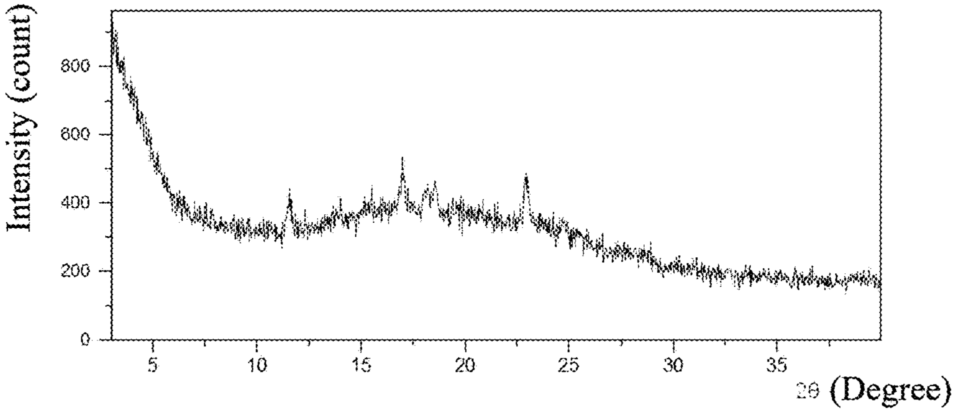
FIG. 14 shows an XRPD pattern of the crystal form B of the 1,5-naphthalene disulfonate of the compound of formula I.
Figure 15:
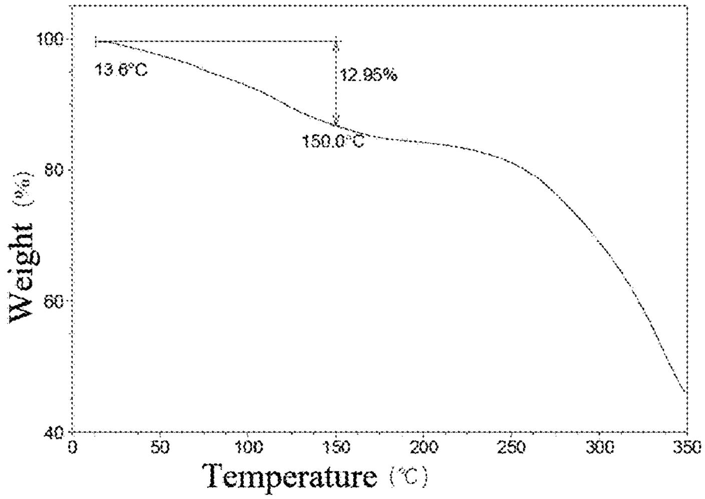
FIG. 15 shows a TGA pattern of the crystal form B of the 1,5-naphthalene disulfonate of the compound of formula I.
Figure 16:
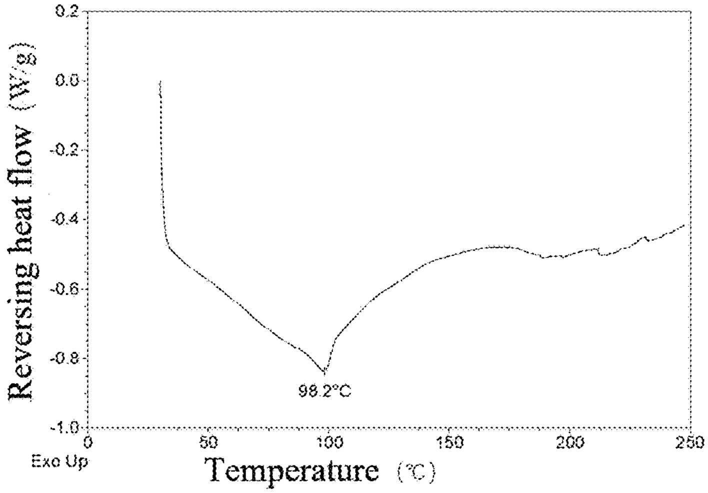
FIG. 16 shows a DSC pattern of the crystal form B of the 1,5-naphthalene disulfonate of the compound of formula I.
Figure 17:
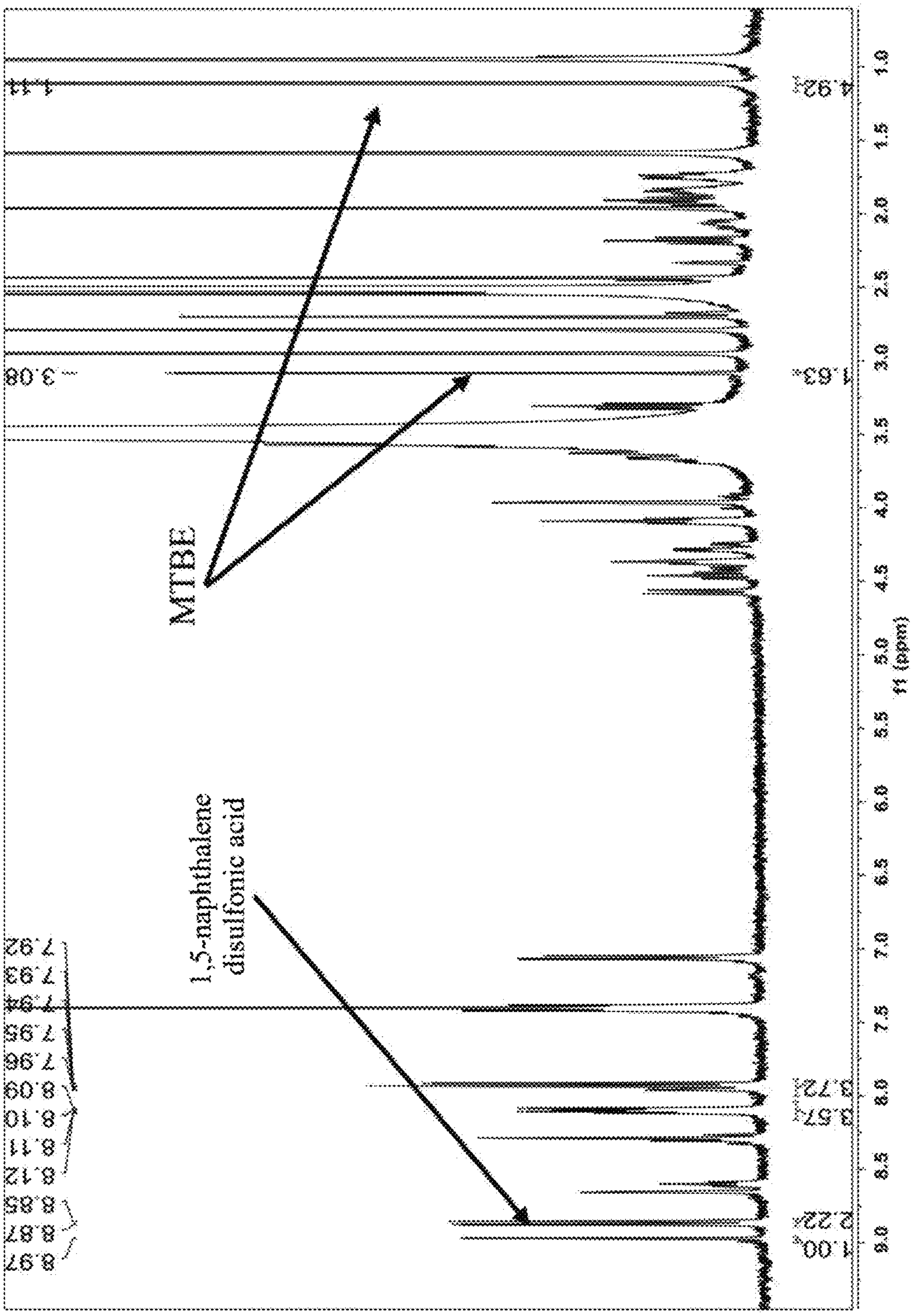
FIG. 17 shows a $^1$H-NMR pattern of the crystal form B of the 1,5-naphthalene disulfonate of the compound of formula I.

The present invention provides a second crystal of the 1,5-naphthalene disulfonate of the compound of formula I, having a crystal form B and having a measured XRPD pattern substantially consistent with FIG. 14, a measured TGA pattern substantially consistent with FIG. 15, a measured DSC pattern substantially consistent with FIG. 16, and a measured d $^1$H-NMR pattern substantially consistent with FIG. 17.

By the XRPD pattern, it can be found that crystal form B has diffraction peaks at 2θ values of: 11.6±0.2°, 17.0±0.2° and 23.0±0.2°.

In the present invention, the crystal can have water adsorbed from the environment, and the water content of the amorphous substance can be, in percentage by weight, about 15.0 wt % or less, preferably about 10.0 wt % or less, for example, about 9.9 wt %.

In the present invention, the crystal can have residual solvent.

The crystal can have, in percentage by weight, about 10.0 wt % or less, preferably about 5.0 wt % or less, for example, 3.1 wt %, of the residual solvent.

In one embodiment of the present invention, the solvent in the crystal can be methyl tert-butyl ether.

In one embodiment of the present invention, the molar ratio of the compound of formula I to the methyl tert-butyl ether in the crystal can be about 1:0.1 to 1.0, such as 1:0.1, 1:0.2, 1:0.3, 1:0.4, 1:0.5, 1:0.6, 1:0.7, 1:0.8, 1:0.9 or 1:1.0.

In one preferred embodiment of the present invention, the molar ratio of the compound of formula I to the methyl tert-butyl ether in the crystal can be about 1:0.5.

By the TGA pattern, it can be found that the crystal shows a weight loss of about 13.0% at 150±3° C.

By the DSC pattern, it can be found that the crystal shows heat absorption at 98±3° C.

In one embodiment of the present invention, the molar ratio of the compound of formula I to the 1,5-naphthalene disulfonic acid in the crystal can be about 1:1.0 to 2.0, such as 1:1.0, 1:1.1, 1:1.2, 1:1.3, 1:1.4, 1:1.5, 1:1.6, 1:1.7, 1:1.8, 1:1.9 or 1:2.0.

In one preferred embodiment of the present invention, the molar ratio of the compound of formula I to the 1,5-naphthalene disulfonic acid in the crystal can be about 1:1.1.

In the present invention, the crystal can be prepared by the steps of: stirring the compound of formula I and 1,5-naphthalene disulfonic acid in methyl tert-butyl ether (for example, stirring at room temperature for 1-5 days, such as 3 days), performing cyclic heating and cooling at least once (the highest temperature in the cyclic heating and cooling is below the boiling point of the solvent, for example, 45° C.-55° C., such as 50° C., and the lowest temperature is above 0° C., such as 5° C.; the number of cycles is 2-5 times, such as 3 times), and separating and drying the solid.

Pharmaceutical Composition and Pharmaceutical Preparation

The present invention provides a pharmaceutical composition, which can comprise at least one of (preferably a preventively, alleviatedly and/or therapeutically effective amount of): an amorphous substance of the compound of formula I or a hydrate of the compound of formula I, a 1,5-naphthalene disulfonate of the compound of formula I, an amorphous substance of the 1,5-naphthalene disulfonate of the compound of formula I, a crystal having a crystal form A of the 1,5-naphthalene disulfonate of the compound of formula I, and a crystal having a crystal form B of the 1,5-naphthalene disulfonate of the compound of formula I.

In the present invention, the above-mentioned pharmaceutical composition can further comprise a pharmaceutically acceptable excipient.

In one embodiment of the present invention, the above-mentioned pharmaceutical composition comprises a preventively, alleviatedly and/or therapeutically effective amount of an amorphous substance of the compound of formula I of the present invention, and at least one pharmaceutically acceptable excipient.

In one embodiment of the present invention, the above-mentioned pharmaceutical composition comprises a preventively, alleviatedly and/or therapeutically effective amount of a 1,5-naphthalene disulfonate of the compound of formula I of the present invention, and at least one pharmaceutically acceptable excipient.

In one embodiment of the present invention, the above-mentioned pharmaceutical composition comprises a preventively, alleviatedly and/or therapeutically effective amount of an amorphous substance of the 1,5-naphthalene disulfonate of the compound of formula I of the present invention, and at least one pharmaceutically acceptable excipient.

In one embodiment of the present invention, the above-mentioned pharmaceutical composition comprises a preventively, alleviatedly and/or therapeutically effective amount of a crystal having a crystal form A of the 1,5-naphthalene disulfonate of the compound of formula I of the present invention, and at least one pharmaceutically acceptable excipient.

In one embodiment of the present invention, the above-mentioned pharmaceutical composition comprises a preventively, alleviatedly and/or therapeutically effective amount of a crystal having a crystal form B of the 1,5-naphthalene disulfonate of the compound of formula I of the present invention, and at least one pharmaceutically acceptable excipient.

The present invention provides a pharmaceutical preparation, which can comprise (preferably a preventively, alleviatedly and/or therapeutically effective amount of) at least one of: an amorphous substance of the compound of formula I or a hydrate of the compound of formula I, a 1,5-naphthalene disulfonate of the compound of formula I, an amorphous substance of the 1,5-naphthalene disulfonate of the compound of formula I, a crystal having a crystal form A of the 1,5-naphthalene disulfonate of the compound of formula I, and a crystal having a crystal form B of the 1,5-naphthalene disulfonate of the compound of formula I, and at least one of the following excipients: a solvent, a solubilizer or surfactant, a gel matrix material and a pH regulator.

In one embodiment of the present invention, the above-mentioned pharmaceutical preparation can be a topical pharmaceutical preparation. In the present invention, it is verified that after administration via skin application, the compound of formula I of the present invention can enter sebaceous glands, but cannot enter blood, indicating that administration of the compound of formula I of the present invention via topical administration (administration via skin application) can effectively avoid systemic exposure to the drug to reduce or avoid side effects caused by oral administration of androgen signaling pathway inhibitors while achieving efficacy.

In one embodiment of the present invention, the above-mentioned pharmaceutical preparation or topical pharmaceutical preparation can be a semi-solid preparation.

In one preferred embodiment of the present invention, the above-mentioned pharmaceutical preparation or topical pharmaceutical preparation can be a gel.

In one more preferred embodiment of the present invention, the above-mentioned gel can comprise a preventively, alleviatedly and/or therapeutically effective amount of an amorphous substance of the compound of formula I of the present invention, and a solvent, a solubilizer or surfactant, a gel matrix material and a pH regulator.

In the above-mentioned gel, the weight percentage of the amorphous substance of the compound of formula I in the gel is 0.1%-10.0%, preferably 0.2%-8.0%, more preferably 0.5%-5.0% (such as 0.5%, 1.0%, 2.0%, 3.0%, 4.0% and 5.0%).

The solvent in the above-mentioned gel can be a combination of any one or more of alcohol solvents with water. The alcohol solvent includes a monohydric alcohol, a dihydric alcohol, a trihydric alcohol, a diol polymer or a monoether thereof, for example, any one of or a combination of some of (dehydrated) alcohol, propylene glycol, polyethylene glycol (preferably PEG4000), diethylene glycol monoethyl ether, glycerin, isopropyl alcohol, benzyl alcohol, lanolin alcohols, butanediol, dipropylene glycol and butanol. The alcohol solvent is preferably any one of or a combination of some of dehydrated alcohol, propylene glycol, glycerin, polyethylene glycol (such as PEG200, PEG300, PEG400 and PEG600), and more preferably a combination of dehydrated alcohol with propylene glycol. When the alcohol solvent is a combination of dehydrated alcohol with propylene glycol, the weight ratio (in parts) of the dehydrated alcohol to the propylene glycol to the water in the mixed solvent formed by the alcohol solvent and water is 30-50:20-55:0-30, preferably 30-40:35-50:20-30 (such as 35:35:30, 30:42:22 and 36:45:27); based on the gel, the weight percentage of the water in the gel is 20%-30%, preferably 22%, 25%, 28%, etc.; if the amount of the water is too much or too little, the above-mentioned gel exhibits unstable character, such as a ground glass character or turbidity caused by the precipitation of the drug substance.

The solubilizer or surfactant in the above-mentioned gel can be any one or more of poloxamer 188, polyoxyethylene 40 hydrogenated castor oil, polyoxyethylene 35 castor oil, span 40, glyceryl mono- and distearate, polyethylene glycol (35) stearate, polyglyceryl-3 distearate and Tween 80, preferably any one or more of poloxamer 188, Tween 80, polyoxyethylene 40 hydrogenated castor oil and polyoxyethylene 35 castor oil, more preferably Tween 80; the weight percentage of the solubilizer or surfactant in the above-mentioned gel is 1%-15%, preferably 2%-10% (such as 3%, 3.5%, 6%, 7%, 7.5%, 8%, 9% and 10%), more preferably 3%-8%. if the amount of the solubilizer or surfactant is too much or too little, the above-mentioned gel exhibits unstable character, such as white opacity or turbidity caused by the precipitation of the drug substance.

The gel matrix material in the above-mentioned gel can be any one or more of sodium carboxymethyl cellulose, methyl cellulose, hydroxypropyl methyl cellulose, hydroxypropyl cellulose, poloxamer 407 and carbomer, preferably carbomer (such as carbomer 971P, carbomer 971P NF, carbomer 974P NF, carbomer 980 NF and carbomer 981 NF), more preferably carbomer 971P; the weight percentage of the gel matrix material in the above-mentioned gel is 0.01%-5.0%; preferably 0.1%-2.0% (such as 0.6%, 0.8%, 1.0% and 2.0%).

The pH regulator in the above-mentioned gel can be any one or more of tromethamine, sodium hydroxide, sodium bicarbonate, ethylenediamine, ethanolamine, diisopropanolamine, ammonia water and triethanolamine, preferably triethanolamine. The pH regulator is used for adjusting the pH value of the above-mentioned gel to 5-8, preferably 6-7.

In one embodiment of the present invention, the above-mentioned gel comprises an amorphous substance of the compound of formula I, a ternary solvent consisting of dehydrated alcohol, propylene glycol and water, a gel matrix material (such as carbomer 971P), a pH regulator (such as triethanolamine), and a solubilizer or surfactant (such as Tween 80). Preferably, the above-mentioned gel comprises, in percentage by weight, 0.5%-5% of the amorphous substance of the compound of formula I and 1%-10% of Tween 80. Further preferably, the above-mentioned gel comprises, in percentage by weight, 0.5% of the amorphous substance of the compound of formula I, 29%-31% of dehydrated alcohol, 42%-44% of propylene glycol, 0.5%-0.7% of carbomer 971P, 0.2%-0.4% of triethanolamine, 3.3%-3.7% of Tween 80 and 20%-24% of water; or, comprises 1.0% of the amorphous substance of the compound of formula I, 29%-31% of dehydrated alcohol, 40%-44% of propylene glycol, 0.5%-0.7% of carbomer 971P, 0.2%-0.4% of triethanolamine, 3.0%-5.0% of Tween 80 and 20%-24% of water; or, comprises 2.0% of the amorphous substance of the compound of formula I, 29%-31% of dehydrated alcohol, 36%-39% of propylene glycol, 0.5%-0.7% of carbomer 971P, 0.2%-0.4% of triethanolamine, 5.5%-8.5% of Tween 80 and 20%-24% of water.

In one embodiment of the present invention, the above-mentioned pharmaceutical preparation or topical pharmaceutical preparation can be a liquid preparation.

In another preferred embodiment of the present invention, the above-mentioned pharmaceutical preparation or topical pharmaceutical preparation can be a topical solution.

In another more preferred embodiment of the present invention, the above-mentioned topical solution can comprise a preventively, alleviatedly and/or therapeutically effective amount of an amorphous substance of the compound of formula I of the present invention, and a solvent; and further comprise a solubilizer or surfactant.

In another more preferred embodiment of the present invention, the above-mentioned topical solution can comprise a preventively, alleviatedly and/or therapeutically effective amount of an amorphous substance of the compound of formula I of the present invention, and a solvent and a solubilizer or surfactant.

In the above-mentioned topical solution, the weight percentage of the amorphous substance of the compound of formula I in the topical solution is 0.1%-10.0%, preferably 0.2%-8.0% (such as 0.2%, 1.0%, 2.0%, 5.0%, 6.0%, 7.0% and 8.0%), more preferably 0.5%-5.0% (such as 0.5%, 1.0%, 2.0%, 3.0%, 4.0% and 5.0%).

The solvent in the above-mentioned topical solution can be a combination of any one or more of alcohol solvents with water. The alcohol solvent includes a monohydric alcohol, a dihydric alcohol, a trihydric alcohol, a diol polymer or a monoether thereof, for example, any one of or a combination of some of (dehydrated) alcohol, propylene glycol, polyethylene glycol (preferably PEG4000), diethylene glycol monoethyl ether, glycerin, isopropyl alcohol, benzyl alcohol, lanolin alcohols, butanediol, dipropylene glycol and butanol. The alcohol solvent is preferably one of or a combination of two or more of dehydrated alcohol, propylene glycol, glycerin and polyethylene glycol, more preferably a combination of dehydrated alcohol with any one of propylene glycol, polyethylene glycol (for example, PEG200, PEG300, PEG400, PEG600, etc., preferably PEG400) and glycerin. When the mixed solvent is a ternary system of dehydrated alcohol, propylene glycol and water, the weight ratio (in parts) of the dehydrated ethanol to the propylene glycol to the water in the mixed solvent is 20-50:10-55:0-40, preferably 30-50:10-50:0-30, more preferably 30-50:20-50:5-30 (such as 30:50:18, 30:50:16 and 35:45:16); when the mixed solvent is a ternary system of dehydrated alcohol, PEG400 and water, the weight ratio (in parts) of the dehydrated alcohol to the PEG400 to the water in the mixed solvent is 30-50:10-50:0-40, preferably 35-50:15-50:0-35; more preferably 35-50:20-45:0-30; when the mixed solvent is a ternary system of dehydrated alcohol, glycerin and water, the weight ratio (in parts) of the dehydrated alcohol to the glycerin to the water in the mixed solvent is 40-50:20-50:0-40, preferably 40-50:30-50:0-40.

The solubilizer or surfactant in the above-mentioned topical solution can be any one or more of poloxamer 188, polyoxyethylene 40 hydrogenated castor oil, polyoxyethylene 35 castor oil, span 40, glyceryl mono- and distearate, polyethylene glycol (35) stearate, polyglyceryl-3 distearate and Tween 80, preferably any one or more of poloxamer 188, Tween 80, polyoxyethylene 40 hydrogenated castor oil and polyoxyethylene 35 castor oil, more preferably Tween 80; the weight percentage of the solubilizer or surfactant in the above-mentioned topical solution is 1%-15%, preferably 1%-10% (such as 1%, 3%, 5% and 7%).

In one embodiment of the present invention, the topical solution comprises an amorphous substance of the compound of formula I, a ternary solvent consisting of dehydrated alcohol, propylene glycol and water, and a solubilizer or surfactant (such as Tween 80). Preferably, the above-mentioned topical solution comprises, in percentage by weight, 0.5%-5% of an amorphous substance of the compound of formula I and 1%-10% of Tween 80. Further preferably, in percentage by weight, the above-mentioned topical solution comprises 0.45%-0.60% of an amorphous substance of the compound of formula I, 34%-38% of dehydrated alcohol, 44%-49% of propylene glycol, 2.5%-3.5% of Tween 80 and 9%-18% of water; or, comprises 0.9%-1.1% of an amorphous substance of the compound of formula I, 34%-38% of dehydrated alcohol, 44%-49% of propylene glycol, 2.5%-3.5% of Tween 80 and 9.0%-18.0% of water; or, comprises 1.9%-2.2% of an amorphous substance of the compound of formula I, 30%-40% of dehydrated alcohol, 46%-50% of propylene glycol, 6.0%-9.0% of Tween 80 and 4.0%-12.0% of water.

Medical Use

The amorphous substance and/or crystals of the compound of formula I (for example, the amorphous substance of the compound of formula I, including amorphous forms such as an amorphous substance of a free alkali, an amorphous substance of a hydrate, and an amorphous substance of a solvate, etc.) or a pharmaceutically acceptable salt thereof (such as 1,5-naphthalene disulfonate) of the present invention or the pharmaceutical composition of the present invention or the pharmaceutical preparation (or topical pharmaceutical preparation) of the present invention can be used for prevention, alleviation and/or therapy of a disease or disorder.

Furthermore, the present invention provides the use of the amorphous substance and/or crystals of the compound of formula I (for example, the amorphous substance of the compound of formula I, including amorphous forms such as an amorphous substance of a free alkali, an amorphous substance of a hydrate, and an amorphous substance of a solvate, etc.) or a pharmaceutically acceptable salt thereof (such as 1,5-naphthalene disulfonate) of the present invention or the pharmaceutical composition of the present invention or the pharmaceutical preparation (or topical pharmaceutical preparation) of the present invention in the preparation of a drug, wherein the drug can be used for prevention, alleviation and/or therapy of a disease or disorder.

In addition, the present invention further provides a method for prevention, alleviation and/or therapy of a disease or disorder, wherein the method comprises administering to an individual in need thereof a preventively, alleviatedly and/or therapeutically effective amount of the amorphous substance and/or crystals of the compound of formula I (for example, the amorphous substance of the compound of formula I, including amorphous forms such as an amorphous substance of a free alkali, an amorphous substance of a hydrate, and an amorphous substance of a solvate, etc.) or a pharmaceutically acceptable salt thereof (such as 1,5-naphthalene disulfonate) of the present invention or the pharmaceutical composition of the present invention or the pharmaceutical preparation (or pharmaceutical preparation) of the present invention.

In one embodiment of the present invention, the disease or disorder comprises at least one of acne, hirsutism, sebaceous gland enlargement, alopecia, asthma, multiple sclerosis, cancer, Kennedy's disease, ciliopathy, cleft palate, diabetes, heart disease, high blood pressure, inflammatory bowel disease, mental retardation, mood disorder, obesity, refractive errors, infertility, Angelman syndrome, Canavan disease, coeliac disease, Charcot-Marie-Tooth disease, cystic fibrosis, Duchenne muscular dystrophy, hemochromatosis, hemophilia, Klinefelter's syndrome, phenylketonuria, polycystic kidney disease, Prader-Willi syndrome, sickle cell disease, Tay-Sachs disease and Turner syndrome. Further, the cancer includes squamous cell carcinoma, basal cell carcinoma and adenocarcinoma; leukemia; benign and malignant lymphomas, especially Burkitt's lymphoma and non-Hodgkin's lymphoma; benign and malignant melanomas; myeloproliferative diseases; sarcoma, including Ewing's sarcoma, hemangioendothelioma, Kaposi's sarcoma, liposarcoma, myosarcoma, peripheral neuroepithelioma, synovial sarcoma, glioma, astrocytoma, oligodendroglioma, ependymoma, glioblastoma, neuroblastoma, ganglioglioma, medulloblastoma, pinealocytoma, meningioma, meningeal sarcoma, neurofibroma and Schwannomas; head and neck cancer, breast cancer, bladder cancer, prostate cancer, cervical cancer, uterine cancer, lung cancer, ovarian cancer, testicular cancer, thyroid cancer, esophageal cancer, pancreatic cancer, gastric cancer, liver cancer, kidney cancer and colon cancer; carcinosarcoma, Hodgkin's disease, Wilms tumor or teratocarcinoma.

The present invention is further described below by particular examples. Unless otherwise stated, instrument devices, reagents, materials, etc. used in the examples below can be acquired by conventional commercial means.

Compound of Formula I

In the present invention, the compound of formula I can be prepared by a method comprising the steps of:

S1:

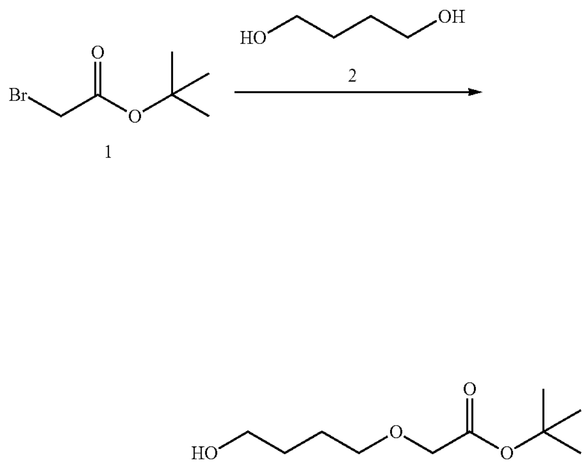

1

2

3

Compound 1 (5.85 g, 0.03 mol), compound 2 (5.4 g, 0.06 mol) and tetrabutyl ammonium chloride (TBAC, 4.17 g, 0.015 mol) were sequentially added to dichloromethane (DCM, 120 mL), after cooling to 0° C., a 33% w/v aqueous sodium hydroxide solution (60 mL) was added dropwise, and a reaction was performed at room temperature overnight. After the reaction was completed, the obtained product was washed with 200 ml of water, extracted with 200 mL of DCM, washed with 100 mL of saturated brine, dried over anhydrous sodium sulfate, spin-dried, and purified by column chromatography (petroleum ether: ethyl acetate=2:1-1:1) to obtain compound 3 (4.08 g, 66.7% yield) as a colorless oil.

S2:

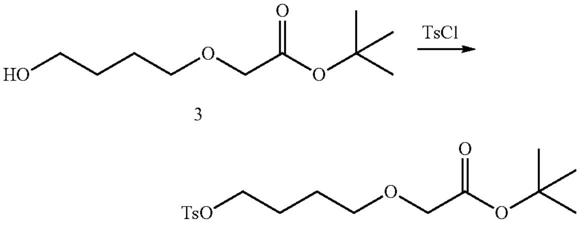

3

4

Compound 3 (4.08 g, 0.02 mmol), p-toluenesulfonyl chloride (TsCI, 5.72 g, 0.03 mol), triethylamine (TEA, 4.04 g, 0.04 mol) and p-dimethylaminopyridine (DMAP, 244 mg, 0.002 mol) were sequentially added to DCM (100 mL), and a reaction was performed at room temperature for 1 h. After the reaction was completed, the obtained product was washed with 100 mL of water, extracted with 100 mL of DCM, washed with 100 mL of saturated brine, dried over anhydrous sodium sulfate, spin-dried, and purified by column chromatography (PE:EA=20:1-10:1) to obtain compound 4 (6 g, 83.7% yield) as a colorless liquid.

S3:

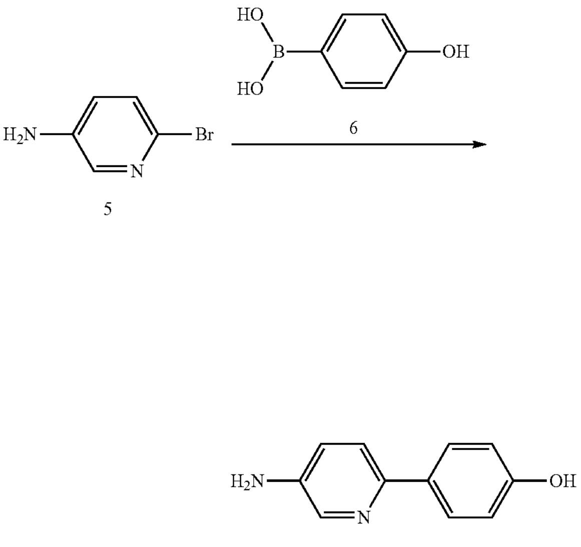

5

6

7

Compound 5 (5.02 g, 0.029 mol), compound 6 (4.83 g, 0.035 mol), [1,1'-bis(diphenylphosphino)ferrocene]dichloropalladium (Pd(dppf)$Cl_2$, 2.12 g, 0.0029 mol) and sodium carbonate ($Na_2CO_3$, 6.15 g, 0.058 mol) were added to dioxane (150 mL) and water (50 mL), and stirred overnight at 90° C. under the protection of $N_2$. After the reaction was completed, the obtained product was filtered, washed with 100 mL of water, extracted with 200 mL of EA 2 times, washed with 100 mL of saturated brine, dried over anhydrous sodium sulfate, spin-dried, and purified by column chromatography (DCM:MeOH=100:1-50:1-20:1) to obtain compound 7 (5.5 g, 92.6% yield) as a brown solid.

S4:

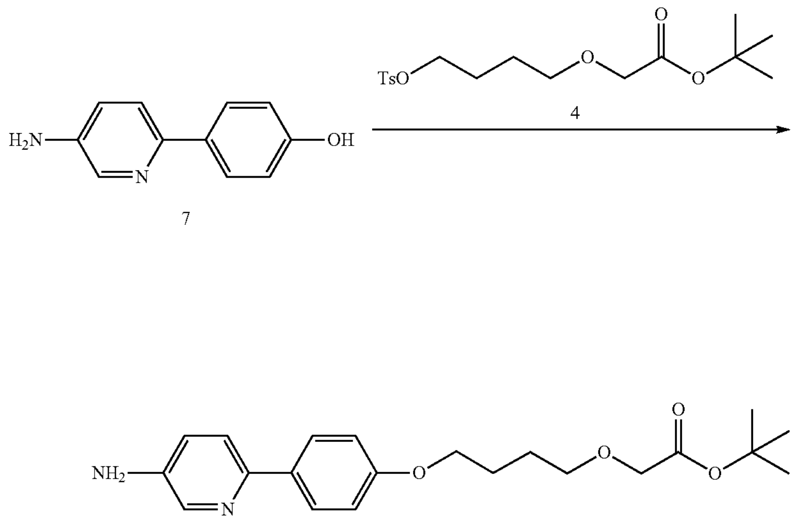

7

4

8

Compound 7 (1.19 g, 9.6 mmol), compound 4 (4.13 g, 11.52 mmol) and potassium carbonate ($K_2CO_3$, 2.65 g, 19.2 mmol) were added to N,N-dimethyl formamide (DMF, 20 mL), and a reaction was performed at 100° C. for 2 h. After the reaction was completed, the obtained product was washed with 100 mL of water, extracted with 100 mL of EA 2 times, washed with 100 mL of saturated brine 2 times, dried over anhydrous sodium sulfate, spin-dried, and purified by column chromatography (PE:EA=5:1-2:1) to obtain compound 8 (2 g, 56% yield) as a light brown oil.

S5:

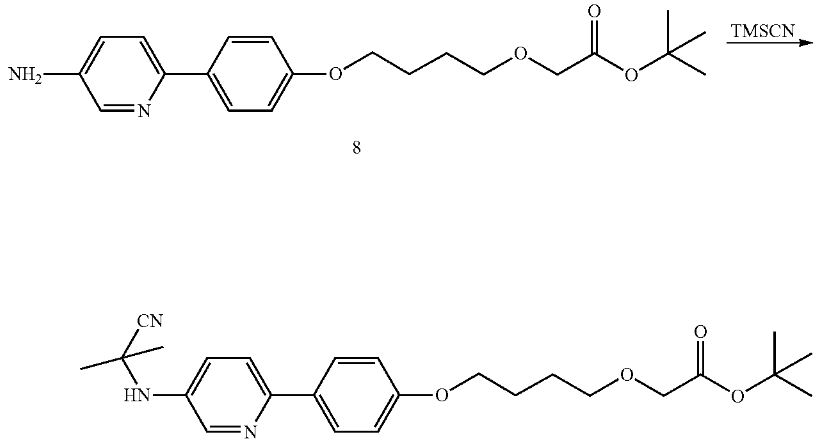

8

9

Compound 8 (2.01 g, 5.4 mmol), trimethylsilyl cyanide (TMSCN, 2.68 g, 27.0 mmol) and zinc chloride ($ZnCl_2$, 147 mg, 1.08 mmol) were sequentially added to acetone (20 mL), and a reaction was performed at room temperature for 1 h. After the reaction was completed, the obtained product was washed with 100 mL of water, extracted with 100 mL of EA, washed with 100 mL of saturated brine, dried over anhydrous sodium sulfate, and spin-dried to obtain compound 9 (2.2 g, 92.8% yield) as a brown oil.

S6:

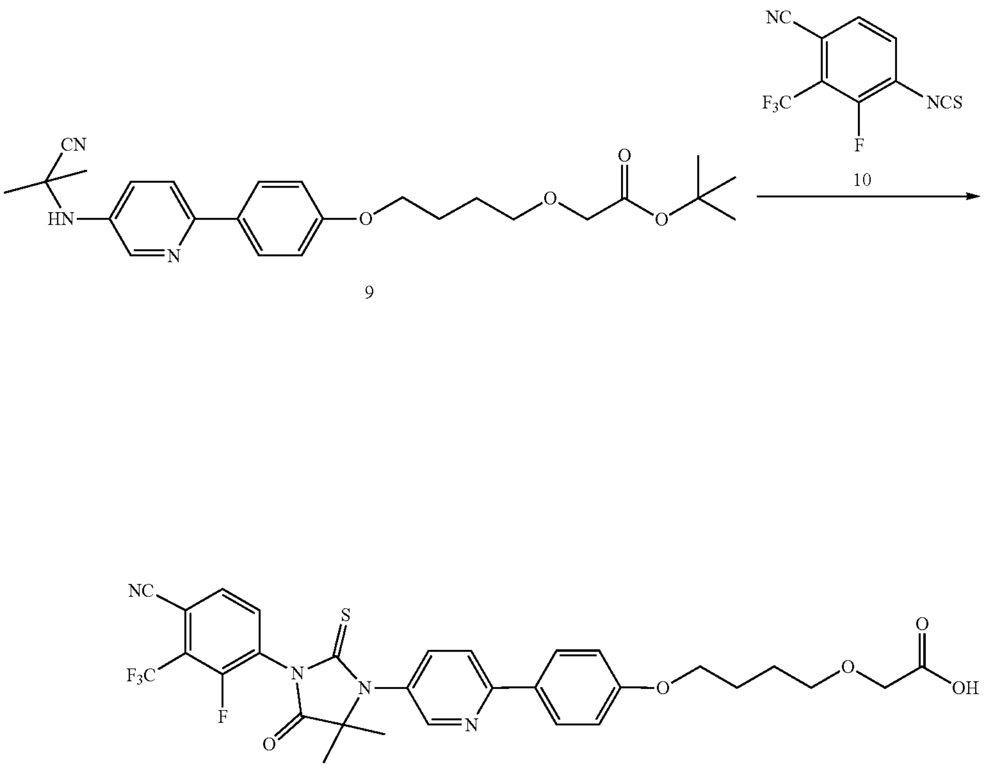

9

10

11

Compound 9 (2.2 g, 5 mmol) and compound 10 (2.46 g, 10 mmol) were added to DMF (20 mL), and stirred at room temperature overnight. Dioxane (20 mL) and 6 N hydrochloric acid (20 mL) were added, and stirred at 90° C. for 1 h. After the reaction was completed, the obtained product was washed with 100 mL of water, extracted with 100 mL of EA 2 times, washed with saturated brine, dried over anhydrous Is sodium sulfate, spin-dried, and purified by column chromatography (PE:EA=5:1-2:1) to obtain compound 11 (1.2 g, 38% yield) as a light brown compound.

S7:

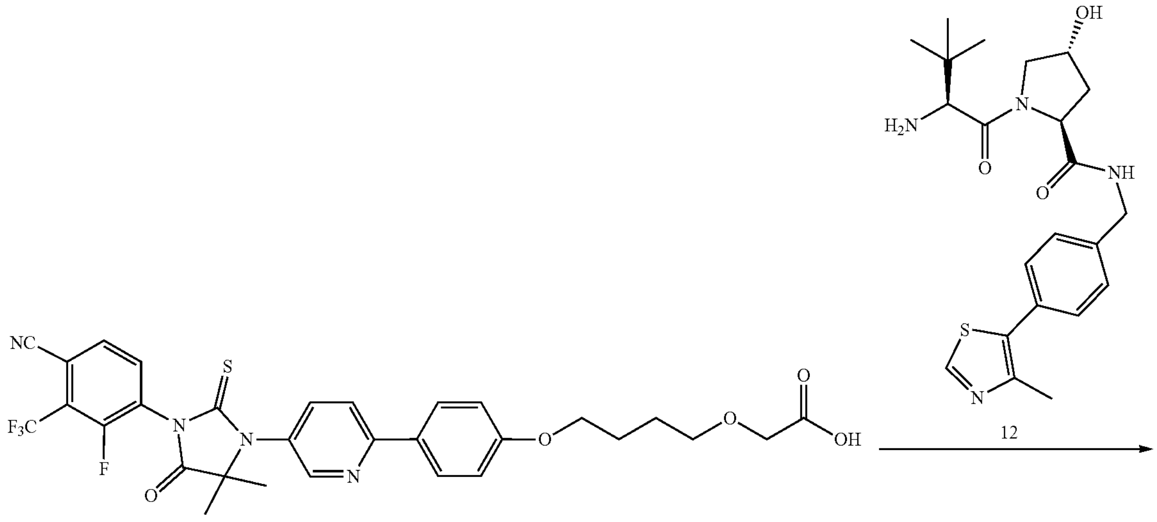

12

11

-continued

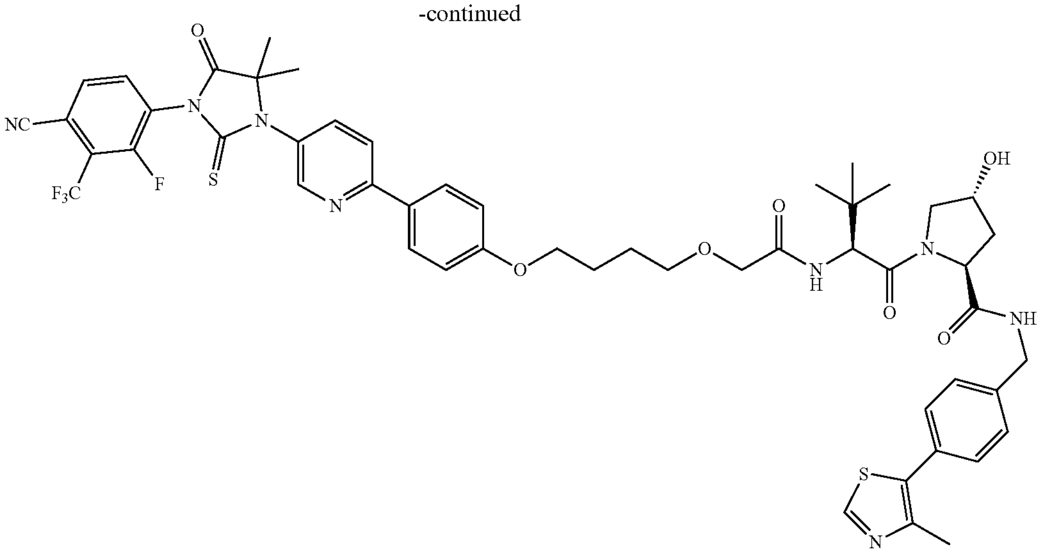

I

Compound 11 (140 mg, 0.22 mmol), compound 12 (103 mg, 0.22 mmol), O-(7-azabenzotriazol-1-yl)-N,N,N',N'-tetramethylurea hexafluorophosphate (HATU, 167 mg, 0.44 mmol) and N,N-diisopropylethylamine (DIEA, 66 mg, 0.66 mmol) were sequentially added to DCM (10 mL), and stirred at room temperature for 1 h. After the reaction was completed, the resulting product was washed with 20 mL of water, extracted with 20 mL of DCM, washed with 20 mL of saturated brine, dried over anhydrous sodium sulfate, spin-dried, and purified by thin-layer chromatography (DCM:MeOH=10:1) to obtain crude product (100 mg). The crude product was purified by preparative column chromatography to obtain the target product (60 mg, 98% purity, 26% yield) as a white solid.

LC-MS: m/z 1043.2 $[M+H]^+$.

$^1$H-NMR (400 MHZ, DMSO-$d_6$): δ 8.97 (d, J=9.7 Hz, 1H), 8.68-8.57 (m, 2H), 8.30 (q, J=8.5 Hz, 2H), 8.10 (dd, J=8.7, 4.1 Hz, 3H), 7.95 (dd, J=8.5, 2.4 Hz, 1H), 7.47-7.36 (m, 5H), 7.06 (d, J=8.9 Hz, 2H), 5.17 (d, J=3.5 Hz, 1H), 4.58 (d, J=9.6 Hz, 1H), 4.50-4.33 (m, 3H), 4.27 (dd, J=15.8, 5.6 Hz, 1H), 4.09 (t, J=6.2 Hz, 2H), 3.96 (s, 2H), 3.70-3.54 (m, 4H), 2.44 (d, J=7.2 Hz, 3H), 2.07 (dd, J=12.4, 8.3 Hz, 1H), 1.95-1.80 (m, 3H), 1.75 (dd, J=13.9, 6.2 Hz, 2H), 1.59 (s, 6H), 0.94 (d, J=6.9 Hz, 9H), the pattern is as shown in FIG. 1.

See CN 202110246427.X for relevant information regarding the compound of formula I.

X-Ray Powder Diffraction (XRPD)

The XRPD patterns were acquired on an PANalytacal Empyrean X-ray powder diffractometer, and the test parameters were as shown in Table 1.

TABLE 1

| XRPD parameters | |
|---|---|
| Parameter | XRPD (reflection mode) |
| X-ray | Cu, kα, kα1 (Å): 1.540598; kα2 (Å): 1.544426; kα2/kα1 intensity ratio: 0.50 |

TABLE 1-continued

| XRPD parameters | |
|---|---|
| Parameter | XRPD (reflection mode) |
| Setting of X-ray light tube | 45 kV, 40 mA |
| Divergent slit | Automatic |
| Scanning mode | Continuous |
| Scanning range (°, 2θ) | 3-40 |
| Scanning step length (°, 2θ) | 0.0167 |

Thermogravimetric Analysis (TGA) and Differential Scanning Calorimetry (DSC)

TGA and DSC/mDSC patterns were acquired on TA Q500/5000 thermogravimetric analyzer and TA Q200/2000/2500 differential scanning calorimeter, respectively and the test parameters were as shown in Table 2 and Table 3.

TABLE 2

| TGA and DSC test parameters | | |
|---|---|---|
| Parameter | TGA | DSC |
| Method | Linear heating up | Linear heating up |
| Sample pan | Aluminum pan, open | Aluminum pan, capped/uncapped |
| Temperature range | Room temperature-set endpoint temperature | 25° C.-set endpoint temperature |
| Scanning rate (° C./min) | 10 | 10 |
| Protective gas | Nitrogen | Nitrogen |

TABLE 3

| mDSC scanning test parameters | |
|---|---|
| Parameter | Setting value |
| Test mode | Conventional mDSC |
| Amplitude | ±1.0° C. |
| Modulation period (seconds) | 60 |
| Scanning rate (° C./min) | 3.0 |

TABLE 3-continued

| mDSC scanning test parameters | |
|---|---|
| Parameter | Setting value |
| Protective gas | Nitrogen |
| Sample pan | Aluminum pan, capped |

Liquid-State Nuclear Magnetic Resonance (Solution NMR)

Liquid-state nuclear magnetic resonance patterns were acquired on Bruker 400M nuclear magnetic resonance spectrometer (DMSO-$d_6$ as the solvent).

Example 1: Preparation of Amorphous Substance of Compound of Formula I

The products were prepared from the compound of formula I as a starting sample by the following methods, and were subjected to XRPD characterization and comparison. The results showed that the products were all amorphous substances and no crystal form was found.

Method 1: Slow Volatilization Method

Specific operations: Different slow evaporation experiments were set up with different solvents. About 15 mg of the compound of formula I was respectively taken and placed in a 3 mL vial, and then 0.5 mL of a solvent was respectively added for dissolving the compound (the undissolved compound was filtered using a 0.45 μm PTFE filter membrane). The vials were sealed using a sealing film (for example, Parafilm), and several (for example, 5) holes were pierced on the sealing film. The vials were placed at room temperature for slow evaporation. After the solvent completely evaporated, the solids were collected and tested by XRPD.

After identification, the amorphous substance of the compound of formula I could be obtained under the conditions of ethanol, isopropyl alcohol, acetone, ethyl acetate, tetrahydrofuran, acetonitrile, chloroform, methanol, isopropyl acetate, 2-methyltetrahydrofuran, 1,4-dioxane, methyl isobutyl ketone or toluene as the solvent.

Method 2: Slow Cooling Method

Specific operations: Different slow evaporation experiments were set up with different solvents. About 15 mg of the compound of formula I was respectively taken and placed in a 3 mL vial, and then 0.5 mL of a solvent was respectively added. The mixed solution was stirred at 50° C. for about 2 h, and then filtered. The supernatant was taken. The resulting supernatant was placed in a biochemical incubator, cooled from 50° C. to 5° C. at a rate of 0.1° C./min, and then kept at a constant temperature. The solids were collected (the samples that did not precipitate out solids were transferred to −20° C. for standing or volatilized at room temperature to obtain solids), and tested by XRPD.

After identification, the amorphous substance of the compound of formula I could be obtained under the conditions of toluene, ethanol/n-heptane (such as at a volume ratio of 1/4), acetone/n-heptane (such as at a volume ratio of 1/4), ethyl acetate/n-heptane (such as at a volume ratio of 1/4), tetrahydrofuran/n-heptane (such as at a volume ratio of 1/4), isopropyl acetate/n-heptane (such as at a volume ratio of 1/2), methanol/water (such as at a volume ratio of 1/4), ethanol/water (such as at a volume ratio of 1/4), acetonitrile/water (such as at a volume ratio of 1/4), tetrahydrofuran/water (such as at a volume ratio of 1/4), isopropyl alcohol/cyclohexane (such as at a volume ratio of 1/9), acetone/cyclohexane (such as at a volume ratio of 1/9) or methyl isobutyl ketone/cyclohexane (such as at a volume ratio of 1/4) as the solvent.

Method 3: Gas-Solid Diffusion Method

Specific operations: Different gas-solid diffusion experiments were set up with different solvents. About 15 mg of the compound of formula I was respectively taken and placed in a 3 mL vial. About 4 mL of a solvent was added to another 20 mL vial. The 3 mL vial was opened and placed in the 20 mL vial, and then the 20 mL vial was sealed. After standing at room temperature for 7 days, the solids were collected and tested by XRPD.

After identification, the amorphous substance of the compound of formula I could be obtained under the conditions of ethanol, isopropyl alcohol, acetone, ethyl acetate, dichloroethane or water as solvent.

Method 4: Gas-Liquid Diffusion Method

Specific operations: About 15 mg of the compound of formula I was respectively taken and placed in a 3 mL vial, and 0.4 mL of a good solvent was added for dissolving the compound (the undissolved compound was filtered using a 0.45 μm PTFE filter membrane). Another 20 mL vial was taken, and about 4 mL of an anti-solvent was added into the vial. The 3 mL vial containing the solution was open and placed in the 20 mL vial, and then the 20 mL vial was sealed and left to stand at room temperature. When solid precipitation was observed, the solids were separated and tested by XRPD.

After identification, the amorphous substance of the compound of formula I could be obtained under the conditions of 1,4-dioxane/n-heptane, methyl isobutyl ketone/cyclohexane, ethyl acetate/methyl tert-butyl ether, or acetonitrile/methyl tert-butyl ether as the good solvent/anti-solvent combination.

Method 5: Suspension Stirring Method

Specific operations: Different suspension stirring experiments were set up with different solvents. About 15 mg of the compound of formula I was respectively taken and placed in a vial, and 0.5 mL of a solvent was added respectively. The prepared suspension was subjected to magnetic stirring (for example, at 1000 rpm) at room temperature (20° C.) for about 7 days or magnetic stirring (for example, at 1000 rpm) under conditions of cyclic heating and cooling, and then centrifuged, and the solids were collected and tested by XRPD.

The results showed that at room temperature (about 20° C.), the amorphous substance of the compound of formula I could be obtained under the conditions of methyl tert-butyl ether, n-heptane, toluene, water, cyclohexane, methanol/toluene ($V_{MeOH}/V_{tol}$=1/9), chloroform/methyl tert-butyl ether ($V_{CHC13}/V_{MTBE}$=1/9), dichloromethane/n-heptane ($V_{DCM}/V_{n\text{-}hept}$=1/9), isopropyl alcohol/cyclohexane ($V_{IPA}/V_{cyc\text{-}hex}$=1/9), tetrahydrofuran/water ($V_{THF}/V_{H2O}$=1/4), methyl isobutyl ketone/toluene ($V_{MIBK}/V_{tol}$=1/9), isopropyl alcohol/methyl tert-butyl ether ($V_{IPA}/V_{MTBE}$=1/9), ethyl acetate/methyl tert-butyl ether ($V_{EtOA}/V_{MTBE}$=1/4), toluene/methyl tert-butyl ether ($V_{tol}/V_{MTBE}$=1/4), acetone/n-heptane ($V_{ACT}/V_{n\text{-}hept}$ =1/9), isopropyl acetate/n-heptane ($V_{IPA}/V_{n\text{-}hept}$=1/9), ethanol/n-heptane ($V_{EIOH}/V_{n\text{-}hept}$=1/9), acetonitrile/cyclohexane ($V_{ACN}/V_{cyc\text{-}hex}$=1/9), ethyl acetate/cyclohexane ($V_{EtOAc}/V_{cyc\text{-}hex}$=1/9), tetrahydrofuran/cyclohexane ($V_{THF}/V_{cyc\text{-}hex}$=1/9), dimethyl sulfoxide/water ($V_{DMSO}/V_{H2O}$=1/4), methanol/water ($V_{MeOH}/V_{H2O}$=1/4) or 1,4-dioxane/water ($V_{Diox}/V_{H2O}$=1/4) as the solvent.

In addition, the amorphous substance of the compound of formula I could be obtained under the conditions of cyclic heating and cooling (50° C.-5° C., 0.1° C./min) and under the conditions of n-heptane, toluene, water, cyclohexane, N,N-dimethylacetamide/water ($V_{DMAc}/V_{H2O}$=1/4), ethanol/water ($V_{EtOH}/V_{H2O}$=1/4), acetone/n-heptane ($V_{ACT}/V_{n-hept}$=1/9), isopropyl acetate/n-heptane ($V_{IPA}/V_{n-hept}$=1/4), ethyl acetate/cyclohexane ($V_{ELOA}/V_{cyc-hex}$=1/4), methyl tert-butyl ether, N-methylpyrrolidone/water ($V_{NMP}/V_{H2O}$1/4), acetonitrile/water ($V_{ACN}/V_{H2O}$=1/4), isopropyl alcohol/water ($V_{IPA}/V_{H2O}$=1/4), isopropyl alcohol/methyl tert-butyl ether ($V_{IPA}/V_{MTBE}$=1/9), acetone/methyl tert-butyl ether ($V_{ACT}/V_{MTBE}$=1/9), 1,4-dioxane/methyl tert-butyl ether ($V_{Diox}/V_{MTBE}$=1/9), toluene/n-heptane ($V_{tol}/V_{n-hept}$ =1/1), ethanol/n-heptane ($V_{EtOH}/V_{n-hept}$=1/4), ethyl acetate/n-heptane ($V_{EtOA}/V_{n-hept}$=1/4), tetrahydrofuran/cyclohexane ($V_{THF}/V_{cyc-hex}$=1/9) or methyl isobutyl ketone/cyclohexane ($V_{MIBK}/V_{cyc-hex}$=1/9) as the solvent.

Method 6: Anti-Solvent Addition Method

Specific operations: Different anti-solvent addition experiments were set up with different good solvent/anti-solvent combinations. About 15 mg of the compound of formula I was respectively taken and placed in a 20 mL vial, and 0.4 mL of a good solvent was added for dissolving the compound. Then an anti-solvent was added dropwise to the clear solution while stirring. When solids were precipitated, the adding dropwise was stopped. The precipitated solids were separated by centrifugation and tested by XRPD.

The results showed that the amorphous substance of the compound of formula I could be obtained under the conditions of acetone/n-heptane, ethyl acetate/n-heptane, ethanol/n-heptane, isopropyl acetate/n-heptane, 1,4-dioxane/n-heptane, tetrahydrofuran/n-heptane, methanol/water, N-methylpyrrolidone/water, acetonitrile/water, tetrahydrofuran/cyclohexane, chloroform/cyclohexane, methyl isobutyl ketone/cyclohexane, ethyl acetate/cyclohexane, 1,4-dioxane/cyclohexane, ethanol/methyl tert-butyl ether, isopropyl acetate/methyl tert-butyl ether, acetone/methyl tert-butyl ether, isopropyl alcohol/water, N,N-dimethylacetamide/water or dimethyl sulfoxide/water as the good solvent/anti-solvent combination.

The XRPD pattern of the amorphous substance of the compound of formula I was as shown in FIG. 2, showing no sharp peaks having clearly identifiable peak positions and showing only one broad and blunt diffraction peak in the range of 5°-25°.

The TGA pattern and the mDSC pattern of the amorphous substance of the compound of formula I were as shown in FIG. 3 and FIG. 4, respectively. It could be seen that when heated to about 150° C., the sample had a weight loss of about 3.0% the weight loss in TGA was derived from the removal/desorption of the moisture adsorbed by the sample in the environment, and the glass transition temperature was about 109.4° C., wherein.

Example 2: Preparation of Amorphous Substance of 1,5-Naphthalene Disulfonate of Compound of Formula I Method: Solution Crystallization Method Specific operations: The compound of formula I as a starting sample and 1,5-naphthalene disulfonic acid (acid/alkali molar ratio of 1:1) were stirred in EtOH (for example, at room temperature). The solid was separated and dried in vacuum (for example, at room temperature) to obtain the product, and the product was tested by XRPD.

The XRPD pattern and detailed data of the amorphous substance of the 1,5-naphthalene disulfonate of the compound of formula I were as shown in FIG. 6, showing no sharp peaks having clearly identifiable peak positions and showing only two broad and blunt diffraction peaks in the range of 5°-25° (in the range of about 5°-12° and about 12°-25°, respectively).

The TGA pattern and the mDSC pattern of the amorphous substance of the 1,5-naphthalene disulfonate of the compound of formula I were as shown in FIG. 7 and FIG. 8, respectively. It could be seen that when heated to about 150° C., the sample had an overall weight loss of about 7.6% (a portion of the weight loss in TGA was derived from the removal of the residual solvent EtOH, corresponding to the weight loss of about 3.3%, and another portion was derived from the removal/desorption of the moisture adsorbed by the sample in the environment, corresponding to the weight loss of about 4.3%), and the glass transition temperature was about 178.4° C.

The $^1$H-NMR pattern of the amorphous substance of the 1,5-naphthalene disulfonate of the compound of formula I was as shown in FIG. 9. It could be seen that the molar ratio of the 1,5-naphthalene disulfonic acid to the compound of formula I in the sample was about 1.0:1, and the molar ratio of the residual solvent EtOH to the compound of formula I was about 1.0:1. The peak (assigned to 1 hydrogen atom in the compound of formula I) at δ 8.98 was selected as the reference peak, and the other peaks were integrated; the actual integral value of the peak (assigned to 2 hydrogen atoms in 1,5-naphthalene disulfonic acid) at δ 8.84-8.87 was 1.90, close to 2, so there was about 1 molecule of the 1,5-naphthalene disulfonic acid corresponding to 1 molecule of the compound of formula I in the sample; the actual integral value of the peak (assigned to 3 hydrogen atoms in EtOH) at δ 1.07-1.04 was 2.91, close to 3, so there was about 1 molecule of the EtOH corresponding to 1 molecule of the compound of formula I in the sample; therefore, the molar ratio of the compound of formula I to the 1,5-naphthalene disulfonic acid to the EtOH was about 1:1.0:1.0.

Example 3: Preparation of Crystal of 1,5-Naphthalene Disulfonate of Compound of Formula I Starting with the compound of formula I, 24 acids (except for hydrochloric acid using 2 feeding ratios of equal mole and two-fold molar equivalent, the other acids all used a feeding ratio of equal mole), such as hydrochloric acid, hydrobromic acid, sulfuric acid, p-toluenesulfonic acid, methanesulfonic acid, L-aspartic acid, maleic acid, phosphoric acid, L-glutamic acid, L-tartaric acid, fumaric acid, citric acid, L-malic acid, succinic acid, adipic acid, 1,5-naphthalene disulfonic acid, 1,2-ethanedisulfonic acid, 2-hydroxyethyl sulfonic acid, 2-naphthalene sulfonic acid, benzenesulfonic acid, oxalic acid, ethanesulfonic acid, mucic acid and glycolic acid, were selected for salt type screening tests in 3 solvent systems such as methyl tert-butyl ether, acetone/n-heptane and isopropyl alcohol/cyclohexane. About 15 mg of the compound of formula I and the corresponding mole of an acid were stirred in 0.5 mL of a solvent at room temperature (for example, at 1000 rpm) for 3 days, then the sample was separated by centrifugation, and the solid was characterized by XRPD. The results showed that the salt having a crystal form could be obtained only after the salt formation with 1,5-naphthalene disulfonic acid in MTBE, with the corresponding crystal form designated as crystal form A.

Method: Solution Crystallization Method

Specific operations: The compound of formula I as a starting sample and 1,5-naphthalene disulfonic acid (acid/alkali molar ratio of 1:1) were stirred in MTBE (for example, at room temperature) for 3 days. The solid was separated and dried in vacuum (for example, at room temperature) to obtain the product, and the product was tested by XRPD.

The XRPD pattern and detailed data of the crystal having the crystal form A of the 1,5-naphthalene disulfonate of the compound of formula I were as shown in FIG. 10 and Table 4.

TABLE 4

| XRPD pattern data corresponding to crystal form A | | |
|---|---|---|
| No. | 2θ (°) | Relative intensity (%) |
| 1 | 12.6 | 52.4 |
| 2 | 15.9 | 28.3 |
| 3 | 16.8 | 100.0 |
| 4 | 18.8 | 30.5 |
| 5 | 23.4 | 15.2 |
| 6 | 23.8 | 23.0 |
| 7 | 25.0 | 32.5 |
| 8 | 25.3 | 42.0 |
| 9 | 27.3 | 26.1 |
| 10 | 29.6 | 13.1 |
| 11 | 38.0 | 9.0 |

The TGA pattern and the DSC pattern of the crystal having the crystal form A of the 1,5-naphthalene disulfonate of the compound of formula I were as shown in FIG. 11 and FIG. 12, respectively. It could be seen that when heated to about 150.0° C., the sample had an overall weight loss of about 11.3% (a portion of the weight loss in TGA was derived from the removal of the residual solvent MTBE, corresponding to the weight loss of about 5.6%, and another portion was derived from the removal/desorption of the moisture adsorbed by the sample in the environment, corresponding to the weight loss of about 5.7%), and showed 2 endothermic peaks at 100.8° C. and 128.9° C. (peak temperatures).

The $^{1}$H-NMR pattern of the crystal having the crystal form A of the 1,5-naphthalene disulfonate of the compound of formula I was as shown in FIG. 13. It could be seen that the molar ratio of the 1,5-naphthalene disulfonic acid to the compound of formula I in the sample was about 1.5:1, and the molar ratio of the residual solvent MTBE to the compound of formula I was about 1.0:1. The peak (assigned to 1 hydrogen atom in the compound of formula I) at δ 8.99 was selected as the reference peak, and the other peaks were integrated; the actual integral value of the peak (assigned to 2 hydrogen atoms in 1,5-naphthalene disulfonic acid) at δ 8.85-8.87 was 2.92 hydrogen atoms, close to 3, so there was about 1.5 molecules of the 1,5-naphthalene disulfonic acid corresponding to 1 molecule of the compound of formula I in the sample; the actual integral value of the peak (assigned to methoxy in MTBE) at δ 3.08 was close to 3.00, so there was about 1 molecule of the MTBE corresponding to 1 molecule of the compound of formula I in the sample; therefore, the molar ratio of the compound of formula I to the 1,5-naphthalene disulfonic acid to the MTBE was about 1:1.5:1.0.

By fine-tuning the above-mentioned method, a crystal having a crystal form B of the 1,5-naphthalene disulfonate of the compound of formula I was also obtained Method: Solution Crystallization Method Specific operations: The compound of formula I as a starting sample and 1,5-naphthalene disulfonic acid (acid/alkali molar ratio of 1:1) were stirred in MTBE (for example, at room temperature) for 3 days, and then further subjected to cyclic heating and cooling (50° C.-5° C.) 3 times. The solid was separated and dried in vacuum (for example, at room temperature) to obtain the product, and the product was tested by XRPD.

The XRPD pattern and detailed data of the crystal having the crystal form B of the 1,5-naphthalene disulfonate of the compound of formula I were as shown in FIG. 14 and Table 5.

TABLE 5

| XRPD pattern data corresponding to crystal form B | | |
|---|---|---|
| No. | 2θ (°) | Relative intensity (%) |
| 1 | 11.6 | 59.3 |
| 2 | 17.0 | 75.5 |
| 3 | 23.0 | 100.0 |

The TGA pattern and the DSC pattern of the crystal having the crystal form B of the 1,5-naphthalene disulfonate of the compound of formula I were as shown in FIG. 15 and FIG. 16, respectively. It could be seen that when heated to about 150.0° C., the sample had an overall weight loss of about 13.0% (a portion of the weight loss in TGA was derived from the removal of the residual solvent MTBE, corresponding to the weight loss of about 3.1%, and another portion was derived from the removal/desorption of the moisture adsorbed by the sample in the environment, corresponding to the weight loss of about 9.9%), and showed 1 endothermic peak at 98.2° C. (peak temperature).

The 1H-NMR pattern of the crystal having the crystal form B of the 1,5-naphthalene disulfonate of the compound of formula I was as shown in FIG. 17. It could be seen that the molar ratio of the 1,5-naphthalene disulfonic acid to the compound of formula I in the sample was about 1.1:1, and the molar ratio of the residual solvent MTBE to the compound of formula I was about 0.5:1. The peak (assigned to 1 hydrogen atom in the compound of formula I) at δ 8.97 was selected as the reference peak, and the other peaks were integrated; the actual integral value of the peak (assigned to 2 hydrogen atoms in 1,5-naphthalene disulfonic acid) at δ 8.85-8.87 was 2.22, close to 2.2, so there was about 1.1 molecules of the 1,5-naphthalene disulfonic acid corresponding to 1 molecule of the compound of formula I in the sample; the actual integral value of the peak (assigned to methoxy in MTBE) at δ 3.08 was 1.63, close to 1.5, so there was about 0.5 molecules of the MTBE corresponding to 1 molecule of the compound of formula I in the sample; therefore, the molar ratio of the compound of formula I to the 1,5-naphthalene disulfonic acid to the MTBE was about 1:1.1:0.5.

Example 4: Distribution of Compound in Sebaceous Glands and Blood of Golden Hamsters 6 male golden hamsters were selected for the experiment, and randomly divided evenly into 2 groups, with three golden hamsters per group. All animals were fasted overnight before administration, and were administered via a route of single application. Sampling was performed at specific time points after administration. Specific information on animal grouping, administration, sampling, etc. were detailed in Table 6.

TABLE 6

| Animal grouping, administration and sampling schemes | | | | | |
|---|---|---|---|---|---|
| | | | Administration dose | | Blood collecting |
| Group | Animal No. | Adminis-tration route | Administration volume (mL) | Drug concentration (mg/mL) | time point (h) |
| 1 | 1, 2, 3 | Single application | 0.02*2 | 30 | 0.25, 0.5, 1, 2, 4, 6, 8 h |
| 2 | 4, 5, 6 | Single application | 0.02*2 | 100 | 0.25, 0.5, 1, 2, 4, 6, 8 h |

1.1 Experimental Method 1.1.1 Preparation of Drug and Administration Dose

The amorphous substance of the compound of formula I was weighed and placed in a 50 mL centrifugal tube. A mixed solvent (consisting of 75% v/v ethanol, 15% v/v glyceryl tri(2-ethylhexanoate) and 10% v/v glycerin) was added. After vortexing, heating was performed at 60° C. until the amorphous substance of the compound of formula I was completely dissolved. The amorphous substances of the compound of formula I in the two groups were prepared at 30 mg/mL and 100 mg/mL, respectively, and stored at room temperature in the dark.

In group 1, each golden hamster had an application dose of 1.2 mg, corresponding to an administration volume of 30 mL/kg. In group 2, each golden hamster had an application dose of 4 mg, corresponding to an administration volume of 100 mL/kg.

1.1.2 Administration Method

During the experiment, the corresponding dose (the unilateral sebaceous gland had an administration volume of about 0.02 mL) of the drug liquid was applied to the bilateral sebaceous glands of all golden hamster.

1.1.3 Observation of Animal Status

Immediately after administration, the animals were observed for abnormal responses. If there was no abnormal response, the animals were observed twice during the experiment; if an abnormal response was found, it should be recorded in time and the number of observations should be increased until the animal returned to normal or the experiment was completed.

1.1.4 Sample Collection and Storage

After administration, blood was collected into blood collection tubes containing a heparin sodium anticoagulant at corresponding time points. Immediately after collection of whole blood, the blood collection tubes were gently shaken and placed on ice, and then centrifuged (4° C., 4000 rpm, 10 min). The supernatant plasma samples (plasma volume ≥100 μL) were collected, and stored in a refrigerator at about −80° C. The plasma samples were collected for 8 h for analysis.

1.2 Experimental Results

The experimental results showed that even in group 2 (administered at a dose of 4 mg), the maximum blood drug concentration at each sampling time point of 0.25, 0.5, 1, 2, 4, 6 and 8 h was only 10.6 ng/ml. When the sampling was performed at the left and right sebaceous gland sites, the average drug concentration after 8 h was 13513 ng/ml in group 1 (i.e., administered at a dose of 1.2 mg), and the average drug concentration after 8 h was 24223 ng/ml in group 2 (i.e., administered at a dose of 4 mg).

Comparing the concentration of the drug in the blood and the concentration of the drug in the sebaceous glands, it could be seen that the compound of formula I of the present invention can enter sebaceous glands, but cannot enter blood, indicating that administration via topical administration (such as administration via skin application) can effectively avoid systemic exposure to the drug to reduce or avoid side effects caused by oral administration of androgen signaling pathway inhibitors while achieving efficacy.

TABLE 7

| Drug concentration in plasma after skin application of compound of formula I (4 mg) to male golden hamsters | | | | | |
|---|---|---|---|---|---|
| Sampling time | Concentration of compound of formula I in plasma | | | | |
| point | Animal No. | | | | Standard |
| (h) | 4 | 5 | 6 | Mean | deviation |
| 0.25 | / | / | / | # | # |
| 0.5 | / | <0 | <0 | # | # |
| 1 | <0 | / | / | # | # |
| 2 | <0 | <0 | 10.6 | 11 | # |
| 4 | <0 | 4.42 | <0 | 4 | # |
| 6 | / | / | / | # | # |
| 8 | / | / | / | # | # |

Notes:
"/" denotes no molecular ion peak detected;
"#" denotes that it cannot be calculated because the divisor is 0.

TABLE 8

| Drug concentration (ng/mL) in sebaceous glands after skin application of compound of formula I (1.2 mg and 4 mg) to male golden hamsters | | | | | | |
|---|---|---|---|---|---|---|
| Animal No. | Collection site | Dose (mg) | Collection time point (h) | Concentration (ng/mL) | Concentration mean (ng/mL) | Standard deviation |
| 1 | Left sebaceous gland | 1.2 | 8 | 7010 | 13513 | 5280.87 |
| | Right sebaceous gland | | 8 | 9170 | | |
| 2 | Left sebaceous gland | | 8 | 10900 | | |
| | Right sebaceous gland | | 8 | 17900 | | |
| 3 | Left sebaceous gland | | 8 | 20400 | | |
| | Right sebaceous gland | | 8 | 15700 | | |

TABLE 8-continued

Drug concentration (ng/mL) in sebaceous glands after skin application of compound of formula I (1.2 mg and 4 mg) to male golden hamsters

| Animal No. | Collection site | Dose (mg) | Collection time point (h) | Concentration (ng/mL) | Concentration mean (ng/mL) | Standard deviation |
|---|---|---|---|---|---|---|
| 4 | Left sebaceous gland | 4 | 8 | 57100 | 24223 | 17184.16 |
| | Right sebaceous gland | | 8 | 26600 | | |
| 5 | Left sebaceous gland | | 8 | 15000 | | |
| | Right sebaceous gland | | 8 | 19900 | | |
| 6 | Left sebaceous gland | | 8 | 8340 | | |
| | Right sebaceous gland | | 8 | 18400 | | |

Example 5: Screening of Solvent Systems in Pharmaceutical Preparation

In this example, the solvent systems in the pharmaceutical preparation were screened. In view of the stability of the product, the amorphous substance of the compound of formula I needs to be in a completely dissolved state in the preparation.

The amorphous substance of the compound of formula I was prepared into supersaturated solutions with different solvents, and oscillated under a room temperature condition (a constant temperature). After oscillating for 24 h, sampling was performed, and the content of the sample was detected by HPLC under condition 1.

Condition 1:

Chromatographic column: C18 (150 mm×4.6 mm×3.5 μm);

Mobile phase: binary mobile phase system, mobile phase A was 0.1% formic acid in water, mobile phase B was acetonitrile;

Elution time: 68 min;

Elution mode: gradient elution (in the gradient elution process, mobile phase A had the maximum volume percentage of 95% and the minimum volume percentage of 10%);

Detection wavelength: 270 nm.

The results of the solubility of the amorphous substance of the compound of formula I in a single solvent were as shown in Table 9.

TABLE 9

Solubility of amorphous substance of compound of formula I in different solvents

| Solvent | 24 h solubility (mg/mL) |
|---|---|
| Water | 0.00 |
| Liquid paraffin | 0.01 |
| Oleic acid | 1.41 |
| Propylene glycol | 11.95 |
| Dehydrated alcohol | >54.48 |
| Glycerin | 0.44 |
| Polyethylene glycol 400 (PEG400) | 16.02 |

It could be seen from the results in Table 9 that the amorphous substance of the compound of formula I was basically insoluble in water, and had great difference in solubility in common solvents. For example, the solubility in liquid paraffin was extremely low, while the solubility in dehydrated alcohol could be greater than 54 mg/mL, and the sample solution was clear (that is, in the single solvents, only dehydrated alcohol could meet the requirements). However, in view of the irritation of ethanol, the conventional amount and the type of a preparation, the amount of ethanol should be limited to 50% V/V or less.

The dissolving capacity of a single solvent for different substances is fixed and limited due to its fixed polarity and dielectric constant; compared with single solvents, mixed solvents having different compositions and different ratios can achieve better solubility for solutes having different polarities due to their different polarities. Therefore, in view of the relatively high solubility of the amorphous substance of the compound of formula I in dehydrated alcohol, the solubility of the compound of formula I in a binary solvent (dehydrated alcohol-water) was investigated, and the results were as shown in Table 10.

TABLE 10

Solubility of amorphous substance of compound of formula I in dehydrated alcohol-water systems at different ratios

| Solvent system % (w/w) | 24 h solubility (mg/mL) |
|---|---|
| Dehydrated alcohol 10%: water 90% | 0.14 |
| Dehydrated alcohol 20%: water 80% | 0.14 |
| Dehydrated alcohol 30%: water 70% | 0.11 |
| Dehydrated alcohol 40%: water 60% | 0.51 |
| Dehydrated alcohol 50%: water 50% | 6.44 |
| Dehydrated alcohol 60%: water 40% | 26.02 |
| Dehydrated alcohol 70%: water 30% | >34.94 |
| Dehydrated alcohol 80%: water 20% | >42.11 |
| Dehydrated alcohol 90%: water 10% | >77.74 |

The results in Table 8 showed that the solubility of the amorphous substance of the compound of formula I increased roughly with the increase of the proportion of dehydrated alcohol. Since the amorphous substance of the compound of formula I was almost insoluble in water, a too high proportion of water could lead to too low solubility; when dehydrated alcohol was used at an amount of 50% w/w, the solubility of the compound of formula I was 6.44 mg/mL, which was far from the requirement of 50 mg/mL.

It has been suggested by the Handbook of Pharmaceutical Excipients (8th edition, page 358) that the ethanol content greater than 50% v/v in the preparation for topical use can cause skin irritation, while the ethanol content in 50% w/w dehydrated alcohol-water systems was greater than 50% v/v already, so it is necessary to further explore the solubility in ternary mixed solvent systems. According to the results of the solubility of the amorphous substance of the compound of formula I in the single solvents and in the binary solvents, three solvent systems, i.e., dehydrated alcohol-propylene glycol-water, dehydrated alcohol-PEG400-water and dehydrated alcohol-glycerin-water, were initially selected for investigation of the solvent composition and component ratio. The amount of the dehydrated alcohol was controlled within 50% v/v, and the results of the solubility of the amorphous substance of the compound of formula I in different ternary solvent systems were as shown in Table 11, Table 12 and Table 13.

TABLE 11

Solubility of amorphous substance of compound of formula I in dehydrated alcohol-propylene glycol-water systems at different ratios

| Solvent system % (w/w) | Solubility (mg/mL) |
|---|---|
| Dehydrated alcohol 10%-propylene glycol 50%-water 40% | 1.49 |
| Dehydrated alcohol10%-propylene glycol 40%-water 50% | 0.54 |
| Dehydrated alcohol 10%-propylene glycol 30%-water 60% | 0.45 |
| Dehydrated alcohol 10%-propylene glycol 20%-water 70% | 0.03 |
| Dehydrated alcohol 10%-propylene glycol 10%-water 80% | 0.00 |
| Dehydrated alcohol 20%-propylene glycol 50%-water 30% | 12.63 |
| Dehydrated alcohol 20%-propylene glycol 40%-water 40% | 3.79 |
| Dehydrated alcohol 20%-propylene glycol 30%-water 50% | 0.44 |
| Dehydrated alcohol20%-propylene glycol 20%-water 60% | 0.08 |
| Dehydrated alcohol 20%-propylene glycol 10%-water 70% | 0.04 |
| Dehydrated alcohol30%-propylene glycol 50%-water 20% | >178.28 |
| Dehydrated alcohol 30%-propylene glycol 40%-water 30% | 25.21 |
| Dehydrated alcohol 30%-propylene glycol 30%-water 40% | 6.39 |
| Dehydrated alcohol 30%-propylene glycol 20%-water 50% | 2.52 |
| Dehydrated alcohol30%-propylene glycol 10%-water 60% | 0.20 |
| Dehydrated alcohol 35%-propylene glycol 50%-water 15% | >188.89 |
| Dehydrated alcohol 35%-propylene glycol 45%-water 20% | >154.31 |
| Dehydrated alcohol 35%-propylene glycol 40%-water 25% | 62.68 |
| Dehydrated alcohol 35%-propylene glycol 35%-water 30% | 52.29 |
| Dehydrated alcohol 40%-propylene glycol 50%-water 10% | >64.56 |
| Dehydrated alcohol 40%-propylene glycol 40%-water 20% | >97.55 |
| Dehydrated alcohol 40%-propylene glycol 30%-water 30% | 49.77 |
| Dehydrated alcohol 40%-propylene glycol 20%-water 40% | 19.47 |
| Dehydrated alcohol 40%-propylene glycol 10%-water 50% | 3.02 |

TABLE 11-continued

Solubility of amorphous substance of compound of formula I in dehydrated alcohol-propylene glycol-water systems at different ratios

| Solvent system % (w/w) | Solubility (mg/mL) |
|---|---|
| Dehydrated alcohol 50%-propylene glycol 50%-water 00% | >96.03 |
| Dehydrated alcohol 50%-propylene glycol 40%-water 10% | >67.83 |
| Dehydrated alcohol 50%-propylene glycol 30%-water 20% | >69.26 |
| Dehydrated alcohol 50%-propylene glycol 20%-water 30% | >77.51 |
| Dehydrated alcohol 50%-propylene glycol 10%-water 40% | 77.72 |

TABLE 12

Solubility of amorphous substance of compound of formula I in dehydrated alcohol-PEG400-water systems at different ratios

| Solvent system % (w/w) | Solubility (mg/mL) |
|---|---|
| Dehydrated alcohol 10%-PEG400 40%-water 50% | 0.28 |
| Dehydrated alcohol 10%-PEG400 30%-water 60% | 0.06 |
| Dehydrated alcohol 10%-PEG400 20%-water 70% | 0.02 |
| Dehydrated alcohol 10%-PEG400 10%-water 80% | 0.01 |
| Dehydrated alcohol 20%-PEG400 40%-water 40% | 7.9 |
| Dehydrated alcohol 20%-PEG400 30%-water 50% | 0.91 |
| Dehydrated alcohol 20%-PEG400 20%-water 60% | 0.16 |
| Dehydrated alcohol 20%-PEG400 10%-water 70% | 0 |
| Dehydrated alcohol 30%-PEG400 40%-water 30% | 89.15 |
| Dehydrated alcohol 30%-PEG400 30%-water 40% | 11.57 |
| Dehydrated alcohol 30%-PEG400 20%-water 50% | 1.95 |
| Dehydrated alcohol 30%-PEG400 10%-water 60% | 0.31 |
| Dehydrated alcohol 35%-PEG400 45%-water 20% | >257.58 |
| Dehydrated alcohol 35%-PEG400 40%-water 25% | >180.9 |
| Dehydrated alcohol 35%-PEG400 35%-water 30% | 116.52 |
| Dehydrated alcohol 35%-PEG400 30%-water 35% | 35.68 |
| Dehydrated alcohol 40%-PEG400 40%-water 20% | >49.14 |
| Dehydrated alcohol 40%-PEG400 30%-water 30% | 110.72 |
| Dehydrated alcohol 40%-PEG400 20%-water 40% | 17.39 |
| Dehydrated alcohol 40%-PEG400 10%-water 50% | 3.35 |
| Dehydrated alcohol 50%-PEG400 40%-water 10% | >48.49 |
| Dehydrated alcohol 50%-PEG400 30%-water 20% | >49.68 |
| Dehydrated alcohol 50%-PEG400 20%-water 30% | >51.47 |
| Dehydrated alcohol 50%-PEG400 10%-water 40% | 25.13 |

TABLE 13

Solubility of amorphous substance of compound of formula I in dehydrated alcohol-glycerin-water systems at different ratios

| Solvent system % (w/w) | Solubility (mg/mL) |
|---|---|
| Dehydrated alcohol 10%-glycerin 30%-water 60% | <0.1 |
| Dehydrated alcohol 10%-glycerin 20%-water 70% | <0.1 |
| Dehydrated alcohol 10%-glycerin 10%-water 80% | <0.1 |
| Dehydrated alcohol 20%-glycerin 50%-water 30% | <0.1 |
| Dehydrated alcohol 20%-glycerin 40%-water 40% | <0.1 |
| Dehydrated alcohol 20%-glycerin 30%-water 50% | <0.1 |
| Dehydrated alcohol 20%-glycerin 20%-water 60% | <0.1 |
| Dehydrated alcohol 20%-glycerin 10%-water 70% | <0.1 |
| Dehydrated alcohol 30%-glycerin 50%-water 20% | 4.08 |
| Dehydrated alcohol 30%-glycerin 40%-water 30% | 2.26 |
| Dehydrated alcohol 30%-glycerin 30%-water 40% | 0.65 |
| Dehydrated alcohol 30%-glycerin 20%-water 50% | 0.14 |
| Dehydrated alcohol 30%-glycerin 10%-water 60% | 0.08 |
| Dehydrated alcohol 40%-glycerin 50%-water 10% | 40.02 |
| Dehydrated alcohol 40%-glycerin 40%-water 20% | 14.70 |
| Dehydrated alcohol 40%-glycerin 30%-water 30% | 8.84 |
| Dehydrated alcohol 40%-glycerin 20%-water 40% | 3.40 |
| Dehydrated alcohol 40%-glycerin 10%-water 50% | 1.58 |
| Dehydrated alcohol 50%-glycerin 50%-water 00% | >74.12 |
| Dehydrated alcohol 50%-glycerin 40%-water 10% | >64.58 |
| Dehydrated alcohol 50%-glycerin 30%-water 20% | >43.6 |
| Dehydrated alcohol 50%-glycerin 20%-water 30% | 23.92 |
| Dehydrated alcohol 50%-glycerin 10%-water 40% | 15.17 |

In the above solubility data, taking the results of the solubility at a solvent ratio of dehydrated alcohol 30%-water 40%-additional solvent 30% as an example, when the additional solvent was PEG400, propylene glycol or glycerin, the solubilization strengths of the additional solvents were ranked as PEG400>propylene glycol >glycerin; moreover, the following trends were generally exhibited: the higher the proportion of dehydrated alcohol or total organic solvent, the higher the solubility; however, from the perspective of the safety of the preparation, the amount of dehydrated alcohol should be reduced as much as possible; from the perspective of the process of the preparation, the proportion of water needed to be increased as much as possible.

To sum up: In the present invention, ethanol/water was used for compounding with a third solvent (such as propylene glycol, glycerin or PEG400) to achieve high solubility of the amorphous substance of the compound of formula I after compounding; it could not only solve the defect of low solubility in single solvent systems or binary solvent systems, but also reduce skin irritation, complying with industry standards.

Example 6: Topical Solution of Compound of Formula I

On the basis of the screening results of the solvent systems in example 5, the overall proportion of organic solvents was reduced as much as possible while ensuring solubility, so the solvent systems of dehydrated alcohol: propylene glycol:water=35:35:30 (mass ratio) and dehydrated alcohol: polyethylene glycol (PEG400): water=35:35:30 (mass ratio) were selected as the basis to prepare a topical solution with 1% (w/w) strength. Method for preparing topical solution: Prescription amounts of dehydrated alcohol, propylene glycol or PEG400, the amorphous substance of the compound of formula I and water in the table below were added and stirred at room temperature until the compound was completely dissolved to obtain the topical solution sample.

By investigating the stability (at high temperature, under accelerated condition) of the topical solutions, the optimal solvent system was selected. The results were as shown in Table 14. Among them, the total impurity content was detected by HPLC under condition 1.

(1) Research of Stability Under a High Temperature Condition:

The topical solution was packaged in a black high-density polyethylene (HDPE) bottle and placed at 60° C. for 30 days. The content of impurities in the topical solution was detected after preparation and on day 10 and day 30 of the experiment, respectively. Before each detection, the sample temperature should be returned to room temperature.

(2) Research of Stability Under an Accelerated Condition:

The topical solution was packaged in a black HDPE bottle and placed under conditions of 40%±2° C., 75%±5% RH for 6 months. The content of impurities in the topical solution was detected after preparation and in the 1st, 2nd, 3rd and 6th months of the experiment, respectively. Before each detection, the sample temperature should be returned to room temperature.

TABLE 14

Topical solutions and stability thereof based on different solvent systems

| Topical solution component | Formulation 1 (wt %) | Formulation 2 (wt %) |
|---|---|---|
| Amorphous substance of compound of formula I | 1.0 | 1.0 |
| Dehydrated alcohol | 35.0 | 30.0 |
| Propylene glycol | 35.0 | 0 |
| PEG400 | 0 | 35.0 |
| Water | 29.0 | 34.0 |
| Total | 100.0 | 100.0 |

Stability investigation

| Condition | | Total impurity (%) | Total impurity (%) |
|---|---|---|---|
| Accelerated condition | 0 day | 0.91 | 0.40 |
| | Acceleration for 1 month | 1.05 | 0.41 |
| | Acceleration for 2 months | 0.90 | 0.63 |

TABLE 14-continued

| | | | |
|---|---|---|---|
| | Acceleration for 3 months | 0.88 | / |
| | Acceleration for 6 months | 1.00 | / |
| High temperature condition | High temperature for 10 days | 0.94 | 0.79 |
| | High temperature for 30 days | 1.07 | 1.57 |

Notes:
Formulation 1 and Formulation 2 used different batches of the amorphous substances of the compound of formula I (consistent impurity profiles);
"/" denotes that the experiment was not performed.

It could be seen from Table 14 that the total impurity of the Formulation 2 (PEG400-containing system) changed significantly, and after 30 days of exposure to high temperature, the total impurity was as high as 1.5%, nearly 4 times the initial total impurity; and after the same investigation under the high temperature condition for 30 days and under the accelerated condition for 6 months, the total impurity of the Formulation 1 (propylene glycol-containing system) did not change significantly, so the topical solution comprising the propylene glycol-containing ternary solvent system was used for preparing the subsequent topical solution.

The Formulation 1 was poured into a HDPE bottle, and a medicinal spray pump was fitted. The sample solution was sprayed on a clean glass slide, and the appearance of the topical solution was observed. It could be observed that the topical solution droplets changed from colorless transparent to white opaque within 1 min when precipitation occurred, probably because the volatilization of dehydrated alcohol reduced the solubility of the drug substance when the product was spread and exposed to air. Therefore, a re-optimization of the ratio of dehydrated alcohol to propylene glycol was considered on the premise of ensuring an initial solubility of 1.0% (w/w).

The inventors used several groups of dehydrated alcohol and propylene glycol at different ratios of 10:89-89:10 (w/w) to prepare topical solution, but it could be observed that the topical solution droplets changed from colorless to white opaque. Then further attempts were made to add a surfactant to the topical solution (preparation method: according to the prescription amount in Table 15, dehydrated alcohol, propylene glycol, a surfactant, the amorphous substance of the compound of formula I and water were stirred until the compound was completely dissolved to obtain the topical solution sample) to improve the character stability of the product, and different kinds of surfactants were investigated (the sample was sprayed on a clean glass slide and the change in the appearance state of the sample over time was observed).

TABLE 15

| Topical solution and appearance state thereof | | | | | | | |
|---|---|---|---|---|---|---|---|
| | Amount of each component in different prescriptions (wt %) | | | | | | |
| Topical solution component | Formulation 3 | Formulation 4 | Formulation 5 | Formulation 6 | Formulation 7 | Formulation 8 | Formulation 9 |
| Amorphous substance of compound of formula I | 5.0 | 5.0 | 5.0 | 5.0 | 1.0 | 1.0 | 1.06 |
| Dehydrated alcohol | 30.0 | 30.0 | 40.0 | 30.0 | 30.0 | 35.0 | 37.23 |
| Propylene glycol | 57.0 | 54.0 | 30.0 | 62.0 | 50.0 | 45.0 | 47.88 |
| Polyoxyethylene 40 hydrogenated castor oil | 1.0 | | | | | | |
| Polyoxyethylene 35 castor oil | | 4.0 | | | | | |
| Poloxamer 188 | | | 1.0 | | | | |
| Tween 80 | | | | 3.0 | 1.0 | 3.0 | 3.19 |
| Water | 7.0 | 7.0 | 24.0 | | 18.0 | 16.0 | 10.64 |
| Total | 100.0 | 100.0 | 100.0 | 100.0 | 100.0 | 100.0 | 100.0 |
| Appearance | After 90 s whitening | After 70 s whitening | After 10 s whitening | After 90 s whitening | After about 2 min whitening | Clear and transparent* | Clear and transparent |

Notes:
*denotes that when the prescription was repeated, the prepared topical solution was turbid.

It could be seen from Table 15 that polyoxyethylene 40 hydrogenated castor oil (RH40), polyoxyethylene 35 castor oil and poloxamer 188 in the Formulation 3 to the Formulation 5 had all reached the maximum daily amount (IIG limit) of pharmaceutical excipients recorded by FDA, but the improvement in the characters of the topical solution after spraying and exposure to air was still not significant. Tween 80 in the Formulation 6 was far from the IIG limit, but it had some effect on maintaining the stability of the topical solution state.

With reference to the prescription composition of the Formulation 6, on the basis of 1% (w/w) topical solution, the effect of the amount of Tween 80 was investigated. As shown for the Formulation 7 and the Formulation 8, when the amount of Tween 80 increased from 1% to 3%, the whitening phenomenon of the topical solution could be obviously improved. However, when the Formulation 8 was repeated, the prepared topical solution was turbid, and no subsequent spraying experiment was performed, indicating that the prescription of the topical solution 8 was unstable and poorly reproducible. Therefore, fine-tuning was performed on the basis of the Formulation 8, and the obtained Formulation 9 was clear and transparent, had a stable appearance, and was suitable for industrial scale-up production. In addition, in the component of the Formulation 9, the concentration of the preparation of 1% was already far less than the solubility of the amorphous substance of the compound of formula I in the ternary system (for example, the solubility under the condition of dehydrated alcohol 35%-propylene glycol 45%-water 20% was greater than 154.31 mg/mL, and the solubility under the condition of dehydrated alcohol 40%-propylene glycol 50%-water 10% was greater than 64.56 mg/mL). Therefore, Tween 80 not only played a role in solubilization in this formulation system, but also played a role in stabilizing physical properties; that is, the function of the surfactant in the formulation system was not limited to solubilization.

In addition, according to the Formulation 8 or Formulation 9, an ordinary person skilled in the art can also prepare topical solutions having a drug substance content (wt %) of 0.5%, 2.0%, 3.0%, 4.0%, 5.0% or other higher content. For example, in percentage by weight, the topical solution having a drug substance content of 0.5% comprises, 0.5% of the amorphous substance of the compound of formula I, 34%-38% of dehydrated alcohol, 44%-49% of propylene glycol, 2.5%-3.5% of Tween 80 and 9%-18% of water; the topical solution having a drug substance content of 1.0% comprises 1.0% of the amorphous substance of the compound of formula I, 34%-38% of dehydrated alcohol, 44%-49% of propylene glycol, 2.5%-3.5% of Tween 80 and 9.0%-18.0% of water; the topical solution having a drug substance content of 2.0% comprises 2.0% of the amorphous substance of the compound of formula I, 30%-40% of dehydrated alcohol, 46%-50% of propylene glycol, 6.0%-9.0% of Tween 80 and 4.0%-12.0% of water. With the increase of dose, the weight percentage of Tween 80 in the topical solution increased, while the amount of some solvents such as ethanol or water was decreased.

Example 7: Gel of Compound of Formula I

On the basis of the screening results of the solvent systems in example 5 and the screening results of the surfactants in example 6, the overall proportion of organic solvents was reduced as much as possible while ensuring solubility, so the solvent system of dehydrated alcohol: propylene glycol:water=35:35:30 (mass ratio) was selected as the basis to prepare a gel with 1% (w/w) strength. Method for preparing gel: firstly, formulation amounts of raw materials (as shown in Table 16) were weighted, the amorphous substance of the compound of formula I and carbomer 971P were stirred in dehydrated alcohol, so that the amorphous substance of the compound of formula I was completely dissolved and carbomer 971P was uniformly dispersed; secondly, propylene glycol and Tween 80 were added and stirred, allowing carbomer 971P to swell initially (for example, the stirring time was between 20 min-60 min), then purified water was added, and the stirring was continued, allowing carbomer 971P to swell fully (for example, the stirring time was between 60 min-600 min); finally, triethanolamine was added to adjust pH, and stirred evenly to obtain the fine and uniform gel sample.

The characters of the gel were investigated (the sample was coated on a glass slide to observe the appearance state of the gel), and the results were as shown in Table 16.

TABLE 16

| Gel and appearance state thereof | | | | |
|---|---|---|---|---|
| Gel Composition | Gel 1 (wt %) | Gel 2 (wt %) | Gel 3 (wt %) | Gel 4 (wt %) |
| Amorphous substance of compound of formula I | 1.0 | 1.0 | 1.0 | 1.0 |
| Dehydrated alcohol | 35.0 | 30.0 | 30.0 | 30.0 |
| Propylene glycol | 35.0 | 45.1 | 40.1 | 42.6 |
| Carbomer 971P | 0.8 | 0.6 | 0.6 | 0.6 |
| Triethanolamine | 0.2 | 0.3 | 0.3 | 0.3 |
| Tween 80 | 0 | 3.0 | 3.0 | 3.5 |
| Water | 28.0 | 20.0 | 25.0 | 22.0 |
| Total | 100.0 | 100.0 | 100.0 | 100.0 |
| Appearance | The sample quickly changed from a transparent gel to a white opaque appearance | The sample was not completely transparent | The sample slowly changed from a transparent appearance to a turbid appearance | Colorless, uniform and transparent appearance |

It could be seen from the results of the Gel 1 and the Gel 2 in Table 16 that after adding a surfactant or solubilizer (Tween 80), the problem of white opacity of the sample due to the precipitation of the drug substance could be solved; after further supplementing a proper amount of purified water to the Gel 2, it was found that the gel became transparent, so the water content in the gel was increased appropriately to obtain the Gel 3; on the basis of the prescription of the Gel 3, the amount of Tween 80 was appropriately increased in the prescription of the Gel 4 to obtain the colorless, uniform and transparent Gel 4, with the appearance and stability meeting the requirements.

The viscosity (detection apparatus: NDS-5S digital rotary viscometer, No.4 rotor; detection method: an appropriate amount of the gel was taken, and slowly added into a measuring cup to prevent the generation of bubbles, the rotating speed was set at 30 rpm, parallel test was performed three times, and the mean value was taken) and the pH value of the Gel 4 were detected, and the viscosity was 5430 mPa's, and the pH value was 6.47. The results showed that the Gel 4 had a suitable viscosity so as to be able to remain on the application area (such as scalp or other skin areas) for a sufficient period of time; the Gel 4 had a pH above 6.0, was slightly acidic, was suitable for skin application, and was used for therapy of acne or alopecia.

In addition, according to the Gel 4, an ordinary person skilled in the art can also prepare gels having a drug substance content (wt %) of 0.5%, 2.0%, 3.0%, 4.0%, 5.0% or other higher content. For example, in percentage by weight, the gel having a drug substance content of 0.5% comprises 0.5% of the amorphous substance of the compound of formula I, 29%-31% of dehydrated alcohol, 42%-44% of propylene glycol, 0.5%-0.7% of carbomer 971P, 0.2%-0.4% of triethanolamine, 3.3%-3.7% of Tween 80 and 20%-24% of water; the gel having a drug substance content of 1.0% comprises 1.0% of the amorphous substance of the compound of formula I, 29%-31% of dehydrated alcohol, 40%-44% of propylene glycol, 0.5%-0.7% of carbomer 971P, 0.2%-0.4% of triethanolamine, 3.0%-5.0% of Tween 80 and 20%-24% of water; the gel having a drug substance content of 2.0% comprises 2.0% of the amorphous substance of the compound of formula I, 29%-31% of dehydrated alcohol, 36%-39% of propylene glycol, 0.5%-0.7% of carbomer 971P, 0.2%-0.4% of triethanolamine, 5.5%-8.5% of Tween 80 and 20%-24% of water. With the increase of dose, the weight percentage of Tween 80 in the gel increased, while the amount of some solvents such as propylene glycol or dehydrated alcohol was decreased.

Experimental Example 1: Investigation of Stability of Amorphous Substance of Compound of Formula I (1) Accelerated Stability and Long-Term Stability Experiments Referring to ICH Q1A stability testing of new drug substances and products, the amorphous substance of the compound of formula I prepared in example 1 was subjected to a long-term stability experiment (experimental condition: 25±2° C., RH 60%±5%) and an accelerated stability experiment (experimental condition: 40±2° C., RH 75%±5%). The purity of the sample at different times was detected by HPLC under condition 2 to evaluate the physicochemical stability of the amorphous substance of the compound of formula I. The results were as shown in Table 18.

Condition 2:

Instruments: Agilent 1260;

Chromatographic column: C18 (150 mm×4.6 mm×3.5 μm);

column temperature: 45° C.;

Mobile phase: binary mobile phase system, mobile phase A was a 10 mM aqueous ammonium acetate solution (preparation method: ammonium acetate was added into purified water, and mixed evenly, and pH value was adjusted to 4.50±0.05 with acetic acid), mobile phase B was acetonitrile;

Elution mode: gradient elution, with specific procedures as shown in Table 17;

flow rate: 1.0 mL/min;

Injection volume: 5 μL;

Detection wavelength: 270 nm;

Data acquisition: OpenLab CDS2 software.

TABLE 17

Gradient elution table

| Time (min) | Mobile phase A (%, V/V) | Mobile phase B (%, V/V) |
|---|---|---|
| 0 | 75 | 25 |
| 10 | 55 | 45 |
| 35 | 25 | 75 |
| 40 | 10 | 90 |
| 45 | 10 | 90 |
| 45.1 | 75 | 25 |
| 50 | 75 | 25 |

TABLE 18

Results of long-term/accelerated stability of amorphous substance of compound of formula I

| Long term | | | |
|---|---|---|---|
| 0 month | 3 months | 6 months | 9 months |
| 99.25% | 99.36% | 99.37% | 99.29% |
| **Acceleration** | | | |
| 0 month | 1 months | 3 months | 6 months |
| 99.25% | 99.41% | 99.35% | 99.36% |

(2) High Temperature Stability Experiment

The amorphous substance of the compound of formula I prepared in example 1 was stored at 60° C. in the dark for 30 days, and the purity percentages were detected by HPLC on day 0, day 5, day 10 and day 30, respectively. The results were as shown in Table 19.

TABLE 19

Results of high temperature stability of amorphous substance of compound of formula I

| | Time | | | |
|---|---|---|---|---|
| | 0 day | 5 days | 10 days | 30 days |
| Purity % | 99.35% | 99.34% | 99.27% | 99.34% |

The experimental results showed that the amorphous substance of the compound of formula I of the present invention exhibited excellent stability whether in the long-term stability experiment, the accelerated stability experiment or the high-temperature stability experiment.

Experimental Example 2: Investigation of Stability of Preparation of Compound of Formula I (1) Freeze-Thaw Experiment The preparation (taking the Formulation 9 or Gel 4 as the test sample) was placed at −20° C. for 48 h, then transferred to 40° C., and then placed for another 48 h. This was a cycle, and 3 cycles were performed. In each cycle, after the sample was taken out, the sample needed to be balanced to room temperature before being transferred to another condition for placement, such as from −20° C. to 40° C., or from 40° C. to −20° C. In each cycle, the final state was observed after the sample was taken out and returned to room temperature, and the content and related substances were detected (by HPLC under condition 1).

(2) Low Temperature Cycling Experiment

The preparation (taking the Formulation 9 or Gel 4 as the test sample) was placed at 5° C. for 48 h, then transferred to 40° C., and then placed for another 48 h. This was a cycle, and 3 cycles were performed. In each cycle, after the sample was taken out, the sample needed to be balanced to room temperature before being transferred to another condition for placement, such as from 5° C. to 40° C., or from 40° C. to 5° C. In each cycle, the final state was observed after the sample was taken out and returned to room temperature, and the content and related substances were detected (by HPLC under condition 1).

(3) Influencing Factor Investigation Experiment

After the preparation (gel or topical solution) was placed at high temperature (50° C.) for 5 days, 10 days and 30 days, the changes in the content of the compound of formula I and related substances were detected. The results were as shown in Table 20 and Table 21.

TABLE 20

Changes in appearance of gel, content of the compound and related substances in influencing factor investigation experiment

| Investigation item | 0 day | High temperature 50° C. 5 days | 10 days | 30 days |
|---|---|---|---|---|
| Appearance | Pale yellow, uniform, transparent | Pale yellow, uniform, transparent | Pale yellow, uniform, transparent | Pale yellow, uniform, transparent |
| Content (%) | 101.0 | 100.2 | 98.1 | 96.8 |
| Total impurity (%) | 0.66 | 0.57 | 0.60 | 1.2 |
| Maximum single impurity (%) | 0.32 | 0.31 | 0.31 | 0.31 |
| pH | 6.56 | 6.14 | 6.23 | 6.26 |
| Viscosity (mPa · s) | 5956 | 5871 | 5615 | 5715 |

TABLE 21

Changes in appearance of topical solution, content of the compound and related substances in influencing factor investigation experiment

| Investigation item | 0 day | High temperature 50° C. 5 days | 10 days | 30 days |
|---|---|---|---|---|
| Appearance | Pale yellow clear liquid | Pale yellow clear liquid | Pale yellow clear liquid | Pale yellow clear liquid |
| Content (%) | 100.3 | 102.0 | 100.1 | 101.1 |
| Total impurity (%) | 0.67 | 0.66 | 0.65 | 0.63 |
| Maximum single impurity (%) | 0.32 | 0.32 | 0.32 | 0.33 |

The experimental results showed that after the freeze-thaw experiment and the low temperature cycling experiment, the appearance character of the gel was stable, and there was no significant change in the content of the compound and the related substances; under the condition of high temperature 50° C., the content of the compound and the impurities remained basically unchanged after 5 days of placing, and with the extension of time, after 30 days of placing, the content of the compound decreased and the related substances increased, but the content of the compound was still as high as 96.8%; within 30 days of placing, the appearance character was stable, and there was no obvious change in the pH and viscosity; and after the freeze-thaw experiment, the low temperature cycling experiment and the influencing factor (high temperature of 50° C.) experiment, the appearance character of the topical solution was stable, and there was no significant change in the content of the compound and the related substances.

The invention claimed is:

1. An amorphous substance of a compound of formula I,

I

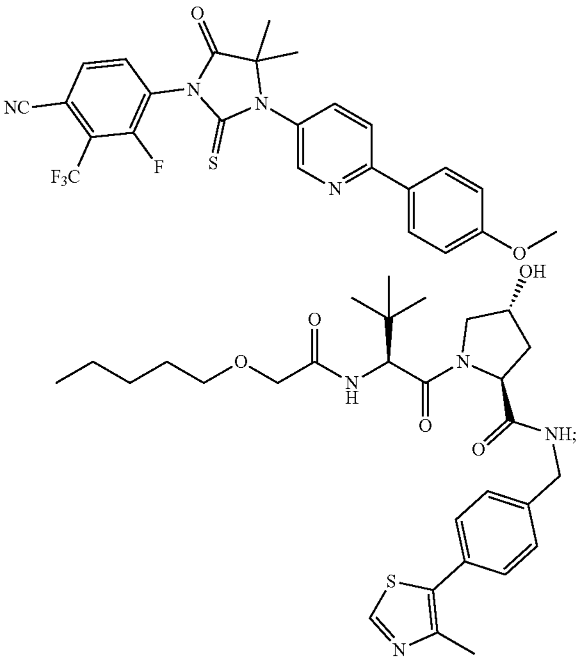

characterized in that the substance has a mDSC pattern showing glass transition temperature of 109.4±3° C.

2. The amorphous substance according to claim 1, characterized in that the amorphous substance has an XRPD pattern that has non-sharp peaks.

3. A 1,5-naphthalene disulfonate of the compound of formula I according to claim 1.

4. An amorphous substance of the 1,5-naphthalene disulfonate of the compound of formula I according to claim 3, characterized in that the amorphous substance has an mDSC pattern showing a glass transition temperature of 178.4±3° C. and the molar ratio of the compound of formula I to 1,5-naphthalene disulfonic acid is about 1:1.

5. The amorphous substance according to claim 4, characterized in that the amorphous substance has an mDSC pattern showing a glass transition temperature of 178.4±3° C.

6. A method for preparing the amorphous substance according to claim 4, characterized in that the method comprises the steps of: stirring the compound of formula I according to claims 1 and 1,5-naphthalene disulfonic acid in ethanol to form a solid, and separating the resulting solid, then drying the resulting solid.

7. A crystal form A of the 1,5-naphthalene disulfonate of the compound of formula I according to claim 3, characterized in that the molar ratio of the compound of formula I to 1,5-naphthalene disulfonic acid is about 1:1.5;

and has an XRPD pattern comprising peaks at 2θ values of: 12.6±0.2°, 16.8±0.2° and 25.3±0.2°.

8. The crystal form A of the 1,5-naphthalene disulfonate of the compound of formula I according to claim 7, characterized in that the crystal form A has a DSC pattern showing heat absorption at 101±3° C. and 129±3° C.

9. A method for preparing the crystal form A according to claim 7, characterized in that the method comprises the steps of: stirring a compound of formula I and 1,5-naphthalene disulfonic acid in methyl tert-butyl ether to form a solid, separating the resulting solid, then drying the resulting solid.

10. A crystal form B of the 1,5-naphthalene disulfonate of the compound of formula I according to claim 3, characterized in that the molar ratio of the compound formula I to 1,5-napthalene disulfonic acid is about 1:1.1;

and has an XRPD pattern comprising peaks of 2θ values of: 11.6±0.2°, 17.0±0.2° and 23.0±0.2°.

11. The crystal form B of the 1,5-naphthalene disulfonate of the compound of formula I according to claim 10, characterized in that the crystal form B has a DSC pattern showing heat absorption at 98±3° C.

12. A method for preparing the crystal form B according to claim 10, characterized in that the method comprises the steps of: stirring the compound of formula I according to claim 1 and 1,5-naphthalene disulfonic acid in methyl tert-butyl ether to form a solid, separating the resulting solid, then drying the resulting solid.

13. A pharmaceutical composition, characterized in that the pharmaceutical composition comprises the amorphous substance according to claim 1, and an optional pharmaceutically acceptable excipient.

14. A pharmaceutical preparation, characterized in that the pharmaceutical preparation comprises the amorphous substance according to claim 1, and at least one of a solvent, solubilizer or surfactant, gel matrix material and pH regulator;

wherein the pharmaceutical preparation is a topical pharmaceutical preparation;

and, the pharmaceutical preparation is a semi-solid preparation;

wherein, the semi-solid preparation is a gel;

wherein, the weight percentage of the amorphous substance in the gel is 0.1%-10.0%;

and, the solvent is a combination of any one or more of alcohol solvents with water;

wherein, the alcohol solvent includes any one of ethanol, propylene glycol, polyethylene glycol, diethylene glycol monoethyl ether, glycerin, isopropyl alcohol, benzyl alcohol, lanolin alcohols, butanediol, dipropylene glycol and butanol, or a combination thereof;

and, the solubilizer or surfactant is any one or more of poloxamer 188, polyoxyethylene 40 hydrogenated castor oil, polyoxyethylene 35 castor oil, span 40, glyceryl mono-and distearate, polyethylene glycol (35) stearate, polyglyceryl-3 distearate and Tween 80;

wherein the weight percentage of the solubilizer or surfactant in the gel is 1%-15%;

and, the gel matrix material is any one or more of sodium carboxymethyl cellulose, methyl cellulose, hydroxypropyl methyl cellulose, hydroxypropyl cellulose, poloxamer 407 and carbomer;

wherein, the amount of the gel matrix material in the gel is 0.01%-5.0%;

and, the pH regulator is any one or more of tromethamine, sodium hydroxide, sodium bicarbonate, ethylenediamine, ethanolamine, ammonia water and triethanolamine;

or, wherein the gel comprises, in percentage by weight, 0.5%-5% of an amorphous substance of the compound of formula I according to claim 1 and 1%-10% of tween 80;

or, wherein the gel comprises, in percentage by weight, 0.5% of an amorphous substance of the compound of formula I according to claim 1, 29%-31% of dehydrated alcohol, 42%-44% of propylene glycol, 0.5%-0.7% of carbomer 971P, 0.2%-0.4% of triethanolamine, 3.0%-3.7% of Tween 80 and 20%-24% of water;

or, wherein the gel comprises, in percentage by weight, 1.0% of an amorphous substance of the compound of formula I according to claim 1, 29%-31% of dehydrated alcohol, 40%-44% of propylene glycol, 0.5%-0.7% of carbomer 971P, 0.2%-0.4% of triethanolamine, 3.0%-5.0% of Tween 80 and 20%-24% of water;

or, wherein the gel comprises, in percentage by weight, 2.0% of an amorphous substance of the compound of formula I, 29%-31% of dehydrated alcohol, 36%-39% of propylene glycol, 0.5%-0.7% of carbomer 971P, 0.2%-0.4% of triethanolamine, 5.5%-8.5% of Tween 80 and 20%-24% of water;

or, the gel comprises, in percentage by weight, 1.0% of an amorphous substance of the compound of formula I according to claim 1, 30.0% of dehydrated alcohol, 42.6% of propylene glycol, 0.6% of carbomer 971P, 0.3% of triethanolamine, 3.5% of Tween 80 and 22.0% of water.

15. A method for preventing, alleviating or treating a disease, comprising administering the amorphous substance according to claim 1 to a subject in need thereof;

wherein, the disease is selected from the group consisting of acne, hirsutism, sebaceous gland enlargement, alopecia, asthma, multiple sclerosis, cancer, Kennedy's disease, ciliopathy, cleft palate, diabetes, heart disease, high blood pressure, inflammatory bowel disease, mental retardation, mood disorder, obesity, refractive errors, infertility, Angelman syndrome, Canavan disease, coeliac disease, Charcot-Marie-Tooth disease, cystic fibrosis, Duchenne muscular dystrophy, hemochromatosis, hemophilia, Klinefelter's syndrome, phenylketonuria, polycystic kidney disease, Prader-Willi syndrome, sickle cell disease Tay-Sachs disease, and Turner syndrome, or a combination thereof;

wherein said cancer comprises squamous cell carcinoma, basal cell carcinoma, adenocarcinoma; leukemia, benign and malignant lymphomas, Burkitt's lymphoma, non-Hodgkin's lymphoma, benign and malignant melanomas;, myeloproliferative diseases, sarcoma, Ewing's sarcoma, hemangioendothelioma, Kaposi's sarcoma, liposarcoma, myosarcoma, peripheral neuroepithelioma, synovial sarcoma, glioma, astrocytoma, oligodendroglioma, ependymoma, glioblastoma, neuroblastoma, ganglioglioma, medulloblastoma, pinealocytoma, meningioma, meningeal sarcoma, neurofibroma, Schwannomas, head and neck cancer, breast cancer, bladder cancer, prostate cancer, cervical cancer, uterine cancer, lung cancer, ovarian cancer, testicular cancer, thyroid cancer, esophageal cancer, pancreatic cancer, gastric cancer, liver cancer, kidney cancer, colon cancer, carcinosarcoma, Hodgkin's disease, Wilms tumor and teratocarcinoma.

16. A method for preventing, alleviating or treating a disease, comprising administering the pharmaceutical preparation according to claim 14 to a subject in need thereof;

wherein, the disease is selected from the group consisting of acne, hirsutism, sebaceous gland enlargement, alopecia, asthma, multiple sclerosis, cancer, Kennedy's disease, ciliopathy, cleft palate, diabetes, heart disease, high blood pressure, inflammatory bowel disease, mental retardation, mood disorder, obesity, refractive errors, infertility, Angelman syndrome, Canavan disease, coeliac disease, Charcot-Marie-Tooth disease, cystic fibrosis, Duchenne muscular dystrophy, hemochromatosis, hemophilia, Klinefelter's syndrome, phenylketonuria, polycystic kidney disease, Prader-Willi syndrome, sickle cell disease, Tay-Sachs disease, Turner syndrome and a combination thereof;

wherein said cancer comprises squamous cell carcinoma, basal cell carcinoma, adenocarcinoma; leukemia, benign and malignant lymphomas, Burkitt's lymphoma, non-Hodgkin's lymphoma, benign and malignant melanomas, myeloproliferative diseases, sarcoma, Ewing's sarcoma, hemangioendothelioma, Kaposi's sarcoma, liposarcoma, myosarcoma, peripheral neuroepithelioma, synovial sarcoma, glioma, astrocytoma, oligodendroglioma, ependymoma, glioblastoma, neuroblastoma, ganglioglioma, medulloblastoma, pinealocytoma, meningioma, meningeal sarcoma, neurofibroma, Schwannomas, head and neck cancer, breast cancer, bladder cancer, prostate cancer, cervical cancer, uterine cancer, lung cancer, ovarian cancer, testicular cancer, thyroid cancer, esophageal cancer, pancreatic cancer, gastric cancer, liver cancer, kidney cancer, colon cancer, carcinosarcoma, Hodgkin's disease, Wilms tumor and teratocarcinoma.

17. The crystal form A of the 1,5-naphthalene disulfonate of the compound of formula I according to claim 7, further characterized in having an XRPD pattern comprising peaks at 2θ values of: 15.9±0.2°, 18.8±0.2°, 25.0±0.2° and 27.3 ±0.2°.

18. The crystal form A of the 1,5-naphthalene disulfonate of the compound of formula I according to claim 7, further characterized in having an XRPD pattern comprising peaks at 2θ values of: 23.4±0.2°, 23.8±0.2°, 29.6±0.2°, and 38.0 ±0.2°.

19. A pharmaceutical preparation, characterized in that the pharmaceutical preparation comprises the amorphous substance according to claim 1, and at least one of a solvent, solubilizer or surfactant, gel matrix material and pH regulator;

wherein, the pharmaceutical preparation is a liquid preparation;

and, the liquid preparation is a topical solution;

wherein, the weight percentage of the amorphous substance according to claim 1 in the topical solution is 0.1%-10.0%;

and, the solvent is a combination of any one or more of alcohol solvents with water;

wherein, the alcohol solvent is any one of ethanol, propylene glycol, polyethylene glycol, diethylene glycol monoethyl ether, glycerin, isopropyl alcohol, benzyl alcohol, lanolin alcohols and butanediol, or a combination thereof;

and, the solubilizer or surfactant is any one or more of poloxamer 188, polyoxyethylene 40 hydrogenated castor oil, polyoxyethylene 35 castor oil, span 40, glyceryl mono-and distearate, polyethylene glycol (35) stearate, polyglyceryl-3 distearate and Tween 80;

wherein the weight percentage of the solubilizer or surfactant in the topical solution is 1%-15%;

or, the topical solution comprises, in percentage by weight, 0.5%-5% of an amorphous substance of the compound of formula I according to claim 1 and 1%-10% of tween 80;

or, the topical solution comprises, in percentage by weight, 0.45%-0.60% of an amorphous substance of the compound of formula I according to claim 1, 34%-38% of dehydrated alcohol, 44%-49% of propylene glycol, 2.5%-3.5% of Tween 80 and 9.0%-18.0% of water;

or, the topical solution comprises, in percentage by weight, 1.9%-1.1% of an amorphous substance of the compound of formula I according to claim 1, 34%-38% of dehydrated alcohol, 44%-49% of propylene glycol, 2.5%-3.5% of Tween 80 and 9.0%-18.0% of water;

or, the topical solution comprises, in percentage by weight, 1.9%-2.2% of an amorphous substance of the compound of formula I according to claim 1, 30%-40% of dehydrated alcohol, 46%-50% of propylene glycol, 6.0%-9.0% of Tween 80 and 4.0%-12.0% of water;

or, the topical solution comprises, in percentage by weight, 1.06% of an amorphous substance of the compound of formula I according to claim 1, 37.23% of dehydrated alcohol, 47.88% of propylene glycol, 3.19% of Tween 80 and 10.64% of water.

* * * * *